(12) United States Patent
Devary et al.

(10) Patent No.: US 9,150,642 B2
(45) Date of Patent: *Oct. 6, 2015

(54) ANTI-KTPAF50 ANTIBODIES AND THEIR USES IN THERAPEUTIC AND DIAGNOSTIC METHODS

(75) Inventors: Orly Devary, Jerusalem (IL); Tamara Sandler, Jerusalem (IL)

(73) Assignee: Two To Biotech Ltd., Jerusalem (IL)

( * ) Notice: Subject to any disclaimer, the term of this patent is extended or adjusted under 35 U.S.C. 154(b) by 287 days.

This patent is subject to a terminal disclaimer.

(21) Appl. No.: 13/380,605

(22) PCT Filed: Jun. 29, 2010

(86) PCT No.: PCT/IL2010/000524
§ 371 (c)(1),
(2), (4) Date: Dec. 23, 2011

(87) PCT Pub. No.: WO2011/001432
PCT Pub. Date: Jan. 6, 2011

(65) Prior Publication Data
US 2012/0100147 A1      Apr. 26, 2012

(30) Foreign Application Priority Data
Jun. 29, 2009   (IL) .......................................... 199618

(51) Int. Cl.
| | |
|---|---|
| *G01N 33/574* | (2006.01) |
| *G01N 33/577* | (2006.01) |
| *C07K 16/18* | (2006.01) |
| *A61K 39/395* | (2006.01) |
| *C07K 14/47* | (2006.01) |

(52) U.S. Cl.
CPC ........... *C07K 16/18* (2013.01); *A61K 39/39533* (2013.01); *A61K 39/39558* (2013.01); *G01N 33/577* (2013.01); *G01N 33/57423* (2013.01); *G01N 33/57484* (2013.01); *C07K 14/4748* (2013.01); *C07K 2316/96* (2013.01); *C07K 2317/73* (2013.01); *G01N 2800/042* (2013.01); *G01N 2800/24* (2013.01); *G01N 2800/28* (2013.01)

(58) Field of Classification Search
None
See application file for complete search history.

(56) References Cited

U.S. PATENT DOCUMENTS

| | | | |
|---|---|---|---|
| 4,376,110 | A | 3/1983 | David |
| 5,444,150 | A | 8/1995 | Inman |
| 7,214,786 | B2 | 5/2007 | Kovalic et al. |
| 2004/0214272 | A1 | 10/2004 | La Rosa |
| 2006/0123505 | A1 | 6/2006 | Kikuchi |
| 2007/0032413 | A1* | 2/2007 | Rosen et al. ................. 514/12 |

FOREIGN PATENT DOCUMENTS

| | | |
|---|---|---|
| EP | 1279724 A2 | 2/2003 |
| WO | 2006046239 A2 | 5/2006 |
| WO | WO 2007098093 A2 * | 8/2007 |
| WO | 2008075349 A1 | 6/2008 |
| WO | 2009083968 A1 | 7/2009 |
| WO | 2011001432 A1 | 1/2011 |

OTHER PUBLICATIONS

Sandler et al, 2010. Recent Advances in Clinical Medicine. 168-173.*
Benjamini et al, 1991. Immunology: A Short Course, 2nd edition, p. 40 only.*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Romanovskis et al. "Preparation of head-to-tail cyclic peptides via side-chain attachment : Implications for library synthesis" J. Peptide Res. 51, 356-374 (1998).
Crozet et al, Synthesis and characterization of cyclic pseudopeptide libraries containing thiomethylene and thiomethylene-sulfoxide amide bond surrogates, Molecular Diversity, 3: 261-276, 1998.
Limal et al., Solid-phase synthesis and on resin cyclization of a disulfide bond peptide and lactam analogues corresponding to the major antigenic site of HIV gp41 protein, J. Peptide Res. 52, 121-129 (1988).
Schultz et al, Prediction of Protein Structure and the Principles of Protein Conformation, Springer-Verlag (1979).
Basic and Clinical Immunology [D. Stites et al. (eds.) (1994) Basic and Clinical Immunology , 8th ed.
GenBank CAM67039.1; Hypothetical protein, conserved [*Leishmania infantum*], Jun. 28, 2007.
GenBank EEB02690.1. Splicing factor, putative [*Toxoplasma gondii*ME49], Nov. 5, 2008.
PCT—International Preliminary Report on Patentability for PCT/IL2010/000524, 6 pages, Jan. 4, 2012.
Harlow and Lane (1988) Antibodies: A Laboratory Manual, Cold Spring Harbor Laboratory, Cold Spring Harbor, NY.
Kohler et al., Continuous cultures of fused cells secreting antibody of predefined specificity, Nature, vol. 256, 1975.
Wahl et al., Improved Radioimaging andTumor Localization with Monoclonal F(ab')2, J Nucl Med 24: 316-325, 1983.

(Continued)

*Primary Examiner* — Zachary Howard
(74) *Attorney, Agent, or Firm* — Roach Brown McCarthy & Gruber, P.C.; Kevin D. McCarthy

(57) ABSTRACT

Polyclonal and monoclonal antibodies which specifically recognize the KTPAF50 protein, and compositions comprising thereof are provided. Also provided are uses of the KTPAF50-specific antibodies, in the diagnosis and therapeutic of conditions such as cancer, autoimmune diseases, graft rejection, neurodegenerative diseases and diabetes.

6 Claims, 19 Drawing Sheets

(56) References Cited

OTHER PUBLICATIONS

Yu et al., Synthesis and Study of Peptides with Semirigid i and i+7 Side-chain Bridges Designed for "alpha"-Helix Stabilization, Bioorganic & Medicinal Chemistry 7 (1999) 161±175.

Valero et al., A comparative study of cyclization strategies applied to the synthesis of head-to-tail cyclic analogs of a viral epitope, J Peptide Kea., 1999. 53, 76-67.

Patel et al., A cyclic peptide analogue of the loop 111 region of platelet derived growth factor-BB is a synthetic antigen for the native protein, J Peptide Res , 1999, 53, 68-74.

Rivier et al., Astressin Analogues (Corticotropin-Releasing Factor Antagonists) with Extended Duration of Action in the Rat, J. Med. Chem. 1998, 41, 5012-5019.

Giblin et al., Design and characterization of "alpha"-melanotropin peptide analogs cyclized through rhenium and technetium metal coordination, Proc. Natl. Acad. Sci. USA vol. 95, pp. 12814-12818, Oct. 1998.

Lanzavecchia et al., Human monoclonal antibodies by immortalization of memory B cells, Current Opinion in Biotechnology 2007, 18:523-528.

Panzone et al., J. Antibiot. (Tokyo), 51, 872-9, 1998.

\* cited by examiner

100µl of α-PRT3 1

100µl of α-PRT3 2

100ng/ml PRT3

500ng/ml PRT3

1000ng/ml PRT3

ANTI-KTPAF50 ANTIBODIES AND THEIR USES IN THERAPEUTIC AND DIAGNOSTIC METHODS

FIELD OF THE INVENTION

The present invention relates to novel antibodies and to their use in therapeutic and diagnostic methods, in particular relating to autoimmune disorders and cancer.

BACKGROUND OF THE INVENTION

All publications mentioned throughout this application are fully incorporated herein by reference, including all references cited therein.

Tissue-specific proteins and their expression levels can be excellent indicators for the organism's health state as well as potential targets for treatment in case of disease.

Diseases which affect human beings may be categorized according to the mechanism of their cause. For example, diseases that have an immunological component or etiology include infectious diseases, acute and chronic inflammatory diseases, cancer, transplantation and autoimmune diseases.

The term inflammatory bowel disease (IBD) covers a group of disorders in which the intestines become inflamed (red and swollen), probably as a result of an immune reaction of the body against its own intestinal tissue, and therefore it is considered an auto-immune disorder.

Two major types of IBD have been described: ulcerative colitis (UC) and Crohn's disease (CD). As the name suggests, ulcerative colitis is limited to the colon (large intestine). Although Crohn's disease can involve any part of the gastrointestinal tract from the mouth to the anus, it most commonly affects the small intestine and/or the colon.

When there is severe inflammation, the disease is considered to be in an active stage, and the person experiences a flare-up of the condition. When the degree of inflammation is less (or absent), the person usually is without symptoms, and the disease is considered to be in remission.

The causes of inflammatory bowel disease are not fully clear. An unknown factor/agent (or a combination of factors) triggers the body's immune system to produce an inflammatory reaction in the intestinal tract that continues without control. As a result of the inflammatory reaction, the intestinal wall is damaged leading to bloody diarrhea and abdominal pain.

Genetic, infectious, immunologic, and psychological factors have all been implicated in influencing the development of IBD. There is a genetic predisposition (or perhaps susceptibility) to the development of IBD. However, the triggering factor for activation of the body's immune system has yet to be identified. Factors that can turn on the body's immune system include an infectious agent (as yet unidentified), an immune response to an antigen (e.g., protein from cow milk), or an autoimmune process. As the intestines are always exposed to things that can cause immune reactions, more recent hypothesis is that there is a failure of the organism to turn off normal immune responses.

IBD is a chronic disease, and affected subjects go through periods in which the disease flares up and causes symptoms, followed by periods of remission, in which symptoms disappear or decrease and good health returns.

Symptoms may range from mild to severe and generally depend upon the part of the intestinal tract involved. They include the following: abdominal cramps and pain; bloody diarrhea; severe urgency to have a bowel movement; fever; loss of appetite; weight loss; anemia (due to blood loss).

Intestinal complications of inflammatory bowel disease include the following: profuse bleeding from the ulcers; perforation (rupture) of the bowel; strictures and obstruction (in persons with Crohn's disease, strictures often are inflammatory and frequently resolve with medical treatment); fixed or fibrotic (scarring) strictures may require endoscopic or surgical intervention to relieve the obstruction. In ulcerative colitis, colonic strictures should be presumed to be malignant (cancerous). Fistulae (abnormal passage) and perianal disease are more common in persons with Crohn's disease. Toxic megacolon (acute nonobstructive dilation of the colon) is a life-threatening complication of ulcerative colitis and requires urgent surgical intervention. The risk of colon cancer in ulcerative colitis begins to rise significantly above that of the general population after approximately 8-10 years of diagnosis. The risk of cancer in Crohn's disease may equal that of ulcerative colitis if the entire colon is involved. The risk of small intestine malignancy is increased in Crohn's disease.

Extraintestinal involvement of IBD refers to complications involving organs other than the intestines. These affect only a small percentage of people with IBD. Persons with IBD may have arthritis, skin conditions, inflammation of the eye, liver and kidney disorders, and bone loss.

Diagnosis of IBD is currently done mainly through a combination of exams and tests, which include: stool examination, fecal occult blood test, complete blood count, electrolyte panel, LFTs (measure alanine transaminase, aspartate transaminase, alkaline phosphatase, albumin, total protein, and bilirubin levels).

Radiology (abdomen X-ray or barium enema, e.g.) and endoscopic procedures (colonoscopy and sigmoidoscopy, e.g.) are also used for the diagnosis of IBD. Clearly, there is still no clear cut diagnostic method for IBD, and there is a need for molecular markers which may serve for differential and specific diagnosis of IBD.

Non-limiting examples of types of cancer include adrenocortical cancer; Malignant melanoma; Non-melanoma skin cancer; Cutaneous T-cell Lymphoma; Kaposi's Sarcoma; Bladder cancer; Colon cancer; Colorectal cancer; Rectal cancer; Neuroectodermal and Pineal cancer; Childhood Brain Stem Glioma; Childhood Cerebellar Astrocytoma; Childhood Cerebral Astrocytoma; Childhood medulloblastoma; Childhood visual pathway Glioma; Meningioma; Mixed Glioma; Oligodendroglioma; Astrocytoma; Ependymoma; Pituitary adenoma; Metastasic Adenocarcinoma; Acoustic neuroma; Paravertebral Malignant teratoma; Breast cancer; Ductal carcinoma; Mammary gland neoplasia; Ovarian cancer; Carcinoid tumour; Cervical cancer; Uterus cancer; Endometrial cancer; Vaginal cancer vulva cancer Gestational Trophoblastic cancer; Fallopian cancer; Uterine sarcoma; Leukemia; Lymphoma (Hodgkin's disease and Non Hodgkin's disease); Neuroblastoma; Retinoblastoma; Soft tissue Sarcomas; Wilm's tumour; Fanconi Anemia; Langerhan's Cells Histiocytosis; Malignant Rhabdoid Tumour of Kidney; Liver cancer; Neuroblastoma; Retinoblastoma; Choriocarcinoma; Endocrine cancers; Endometrial cancer; Esophageal cancer; Ewing's Sarcoma; Eye cancer; Gastric cancer; Gastrointestinal cancers; Genitourinary cancers; Glioma; Gynecological cancers; Head and neck cancer; Hepatocellular cancer; Hypopharynx cancer; Islet call cancer; Kidney cancer; Laryngeal cancer; Lung cancer; Lymphoma; Male breast cancer; Melanoma; Mesothelioma; Myeloma, multiple; Nasopharyngeal cancer; Non-melanoma Skin cancer; Esophageal cancer; Osteosarcoma; Ovarian cancer; Pancreas cancer; Pituitary cancer; Prostate cancer; Renal cell carcinoma; Retinoblastoma; Rhabdomyosarcoma; Sarcoma; Skin cancer; Squamous cell carcinoma; Stomach cancer; Testicular cancerthymus cancer; Thyroid cancer; Transitional cells cancer; Trophoblastic cancer; Uterus cancer; Acute Lymphatic leukemia; Acute myeloid leukemia; Adenocystic carcinoma; Anal cancer; Bone cancer; Bowel cancer; Ductal carcinoma; Liposarcoma; Neuroblastoma; Nephroblastoma and Osteosarcoma.

Inflammatory diseases include sepsis, endotoxemia, pancreatitis, uveitis, hepatitis, peritonitis, keratitis, SIRS and injury-induced inflammation.

Diseases linked to fertility include male infertility and female infertility. Male infertility can be caused by a variety of problems. Some of the more common disorders are listed below:

Deficient Sperm Production: Ninety percent of male infertility is caused by the failure to produce enough sperm. Azzospermia occurs when no sperm is produced while oligospermia is diagnosed when few sperm are produced;

Varicocele;

Other Disorders: Other disorders that can cause male infertility include abnormal development or damage of the testes (caused by endocrine disorders or inflammation), disorders of accessory glands, coital disorders, exposure to diethylstilbestrol (DES) a synthetic estrogen used in the 1950's and 1960's that caused cysts in the male reproductive tract, undescended testicles, and in rare cases genetic disorders such as a chromosomal abnormality.

Female infertility can also be caused by a variety of problems. Some of the more common disorders are Polycystic Ovarian Disease, Pelvic Inflammatory Disease, Ovulatory Dysfunction, Uterine Fibroids, Endometriosis, and Immunological Infertility.

Disorders of carbohydrate metabolism occur in many forms. The most common disorders are acquired. Acquired or secondary derangements in carbohydrate metabolism, such as diabetic ketoacidosis, hyperosmolar coma, and hypoglycemia, all affect the central nervous system. Many forms and variants of peripheral nerve disease also are seen in diabetes. The remaining disorders of carbohydrate metabolism are the rare inborn errors of metabolism (i.e. genetic defects).

The acquired disorders of carbohydrate metabolism are fairly common, both in the United States and internationally. Hypoglycemia is a common cause of neurological disease, especially acute mental deterioration, memory loss, disorientation, obtundation, and coma, among both alcoholics and patients with diabetes who are treated with insulin. Hyperinsulinemia from other causes is rare, but pancreatic tumors could be the cause. Diabetes, with its various neurological complications, is among the most common disorders treated in adult patients.

The inherited disorders of carbohydrate metabolism are rare. Severe defects of the pyruvate dehydrogenase (PDH) complex and the benign chemical anomaly called pentosuria have been reported in very few (2-6) patients.

Hypoglycemia, diabetic ketoacidosis, and hyperosmolar coma are all potentially fatal but potentially curable conditions.

In WO 2009/083968 the present inventors described a protein, denominated KTPAF50, which was shown to be specifically expressed in the placenta, kidney (adult and fetal), pancreas and testis, while in the hematopoietic tissue this protein was detected in resting and activated $CD8^+$ cells, resting and activated mononuclear cells, as well as in resting and activated $CD19^+$ cells.

Surprisingly, upon developing specific antibodies to KTPAF50, the inventors show, in the present invention, that expression of KTPAF50 may be correlated with specific disease states, particularly in cancer and autoimmune disorders.

Even more unexpectedly, the present inventors show that KTPAF50-specific antibodies are potent regulators of cell growth and cytokine expression.

Therefore, it is an object of the present invention to provide antibodies which specifically recognize KTPAF50, as well as their uses in diagnosis and treatment of cancer, autoimmune disorders, graft rejection, neurodegenerative diseases and diabetes.

As will be shown by the specification and the following Examples, the diagnostic method of the invention is particularly suitable for detection and monitoring of certain types of cancer and autoimmune disorders.

These and other uses and objects of the invention will become apparent as the description proceeds.

SUMMARY OF THE INVENTION

In a first aspect, the present invention relates to an antibody which specifically recognizes the KTPAF50 protein or any fragments or derivatives thereof, as well as to a composition comprising thereof. Said KTPAF50 protein is denoted by SEQ. ID. NO. 1 or SEQ. ID. NO. 2.

The invention also relates to an antibody which specifically recognizes a KTPAF50-derived peptide, said peptide being denoted by any one of SEQ. ID. NO. 3, SEQ. ID. NO. 5, SEQ. ID. NO. 6 and SEQ. ID. NO. 7, as well as to a composition comprising thereof.

The antibodies as described herein or a composition comprising thereof, are for use in diagnostic and/or therapeutic methods.

In particular, said antibodies or a composition comprising thereof are for use in the diagnosis or prognosis of one of cancer and autoimmune disorders, as well as in the treatment of cancer.

In another aspect the present invention provides an antibody-producing cell line, or a hybridoma cell line, wherein said cell line produces an antibody which specifically recognizes the KTPAF50 protein or a peptide derived therefrom. Antibodies produced by these cell lines are also provided by the present invention.

In a further aspect, the present invention provides the use of an antibody which specifically recognizes the KTPAF50 protein or a peptide derived therefrom, in the preparation of a diagnostic or a therapeutic composition.

In one embodiment, the diagnostic composition provided herein is for the diagnosis of any one of cancer and autoimmune disease.

The therapeutic composition as provided by the present invention is for the treatment of a condition selected from the group consisting of cancer, autoimmune diseases, neurodegenerative diseases, diabetes and graft rejection.

In a further aspect, the present invention provides a method for the diagnosis of any one of cancer or an autoimmune disease in a subject, said method comprising the steps of:
a) provided a sample from said subject;
b) contacting said sample with at least one antibody which specifically recognizes the KTPAF50 protein or a peptide derived therefrom or with a composition comprising thereof;
c) detecting the formation of a complex between said at least one antibody and its specific antigen, through detection means;
whereby the detection of a complex indicates that said subject suffers from cancer or an autoimmune disorder.

In one embodiment of said method, said sample is a blood sample.

In another particular embodiment of said method said cancer is selected from the group consisting of lung, breast and ovarian cancer.

In a further embodiment the present invention provides a method for the treatment of cancer, said method comprising administering a therapeutically effective amount of at least one anti-KTPAF50 antibody or a combination thereof, or a composition comprising thereof, to a subject in need.

The present invention further provides a method of inhibiting cell growth or inhibiting cytokine expression, said method comprising contacting an effective amount of at least one anti-KTPAF50 antibody or a combination thereof, or a composition comprising thereof, with cells. In one particular embodiment, said cells are cells that express cytokines.

Particular cytokines whose expression is inhibited by the antibodies of the invention are TNF-α, IFN-γ or IL-10.

In a further aspect the present invention provides a kit for any one of diagnosis, monitoring treatment efficacy or assessing prognosis of cancer or an autoimmune disease, said kit comprising the following components:
a) at least one antibody according to the invention or a composition comprising thereof; and
b) instructions for carrying out the detection of the presence of an antigen in a sample, wherein said antigen is specifically recognized by said antibody of the invention.

Said kit may further comprise at least one of the following components:
a) at least one means for collecting a sample to be tested;
b) at least one reagent necessary for detection of said recognition of said antigen by said antibody; and
c) at least one control sample.

BRIEF DESCRIPTION OF THE FIGURES

FIG. 3A: Histogram showing the effect of 24-hour treatment with anti-KTPAF50 antibody measured after 4-hour incubation with Resazurin.

FIG. 3B: Histogram showing the effect of 24-hour treatment with anti-KTPAF50 antibody measured after 24-hour incubation with Resazurin.

FIG. 3C: Histogram showing the effect of 48-hour treatment with anti-KTPAF50 antibody measured after 24-hour incubation with Resazurin. Abbreviations: anti-PRT3 1=antibody 3E3G7; anti-PRT3 2=antibody 5E11H3; Treat.=treatment; rel. cont.=relative to control.

FIG. 4A: Histogram showing the effect of 24-hour treatment with anti-KTPAF50 antibody measured after 24-hour incubation with Resazurin, in cells from male C57/black mouse.

FIG. 4B: Histogram showing the effect of 24-hour treatment with anti-KTPAF50 antibody measured after 24-hour incubation with Resazurin from female C57/black mouse.

FIG. 4C: Histogram showing the effect of 48-hour treatment with anti-KTPAF50 antibody measured after 24-hour incubation with Resazurin, in cells from male C57/black mouse.

FIG. 4D: Histogram showing the effect of 48-hour treatment with anti-KTPAF50 antibody measured after 24-hour incubation with Resazurin from female C57/black mouse.

FIG. 4E: Histogram showing the effect of 72-hour treatment with anti-KTPAF50 antibody measured after 4.5-hour incubation with Resazurin, in cells from male C57/black mouse.

FIG. 4F: Histogram showing the effect of 72-hour treatment with anti-KTPAF50 antibody measured after 4.5-hour incubation with Resazurin from female C57/black mouse.

Abbreviations: anti-PRT3 1=antibody 5E11H3; anti-PRT3 2=antibody 3E3G7; Treat.=treatment; rel. cont.=relative to control.

Figure 5:
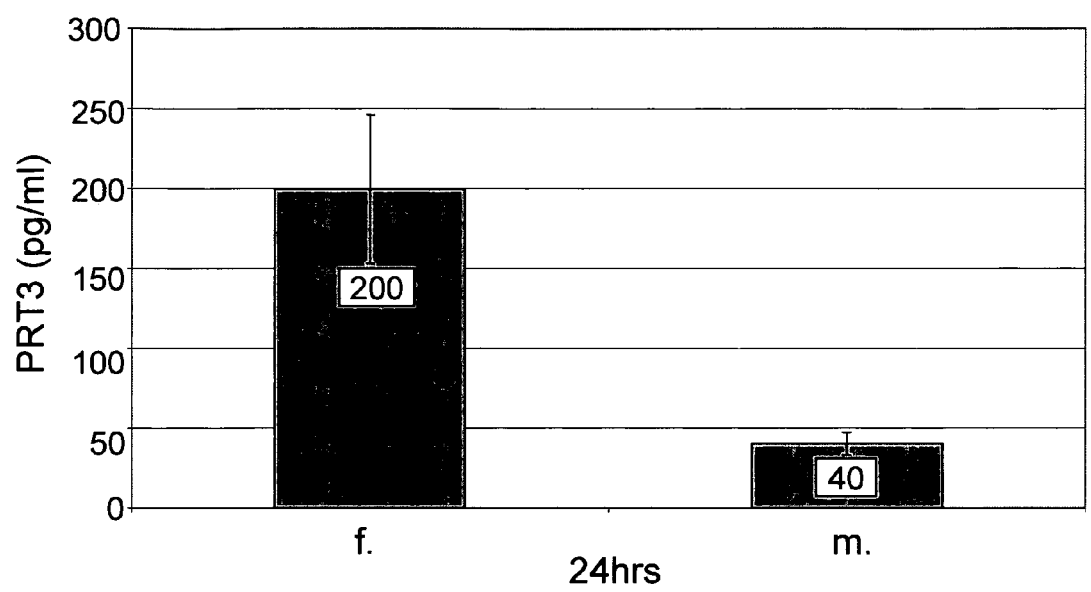

FIG. 5: KTPAF50 concentration in medium from C57/black treated splenocytes.

Abbreviations: f.=female; m.=male

Figure 6A:
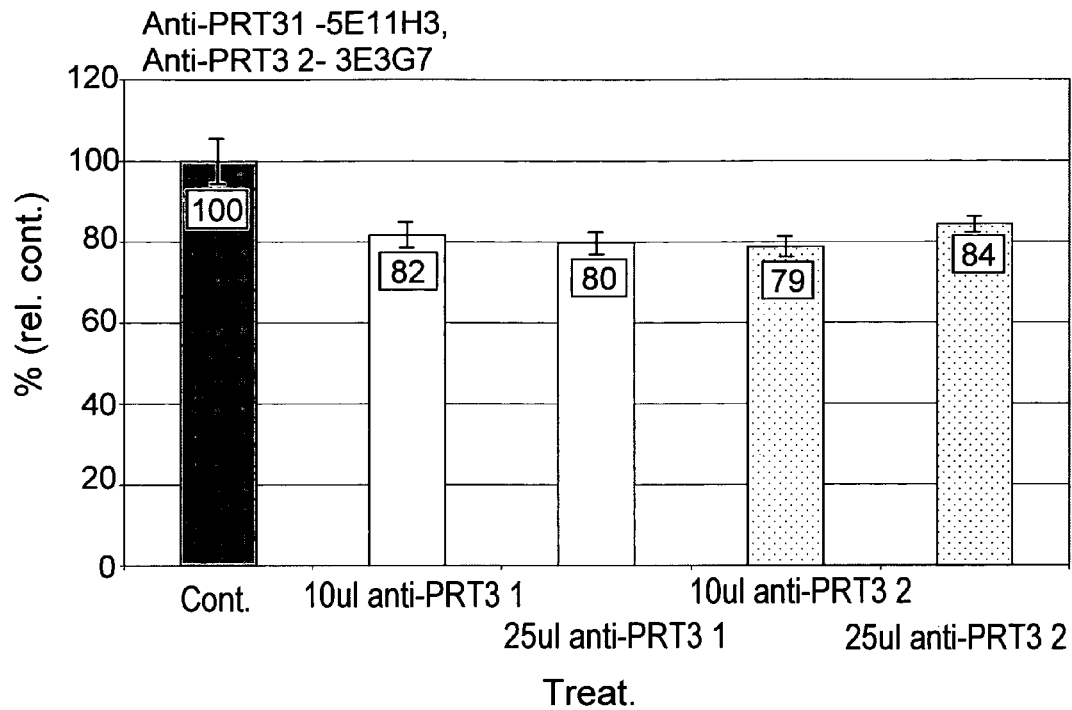
Figure 6B:
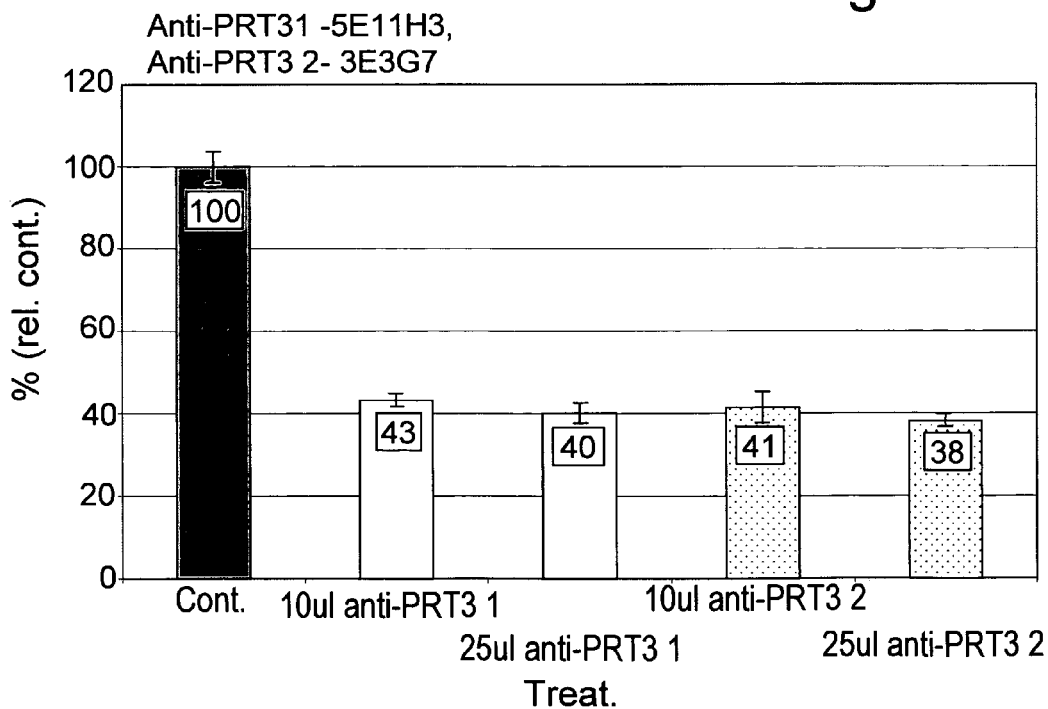
Figure 6C:
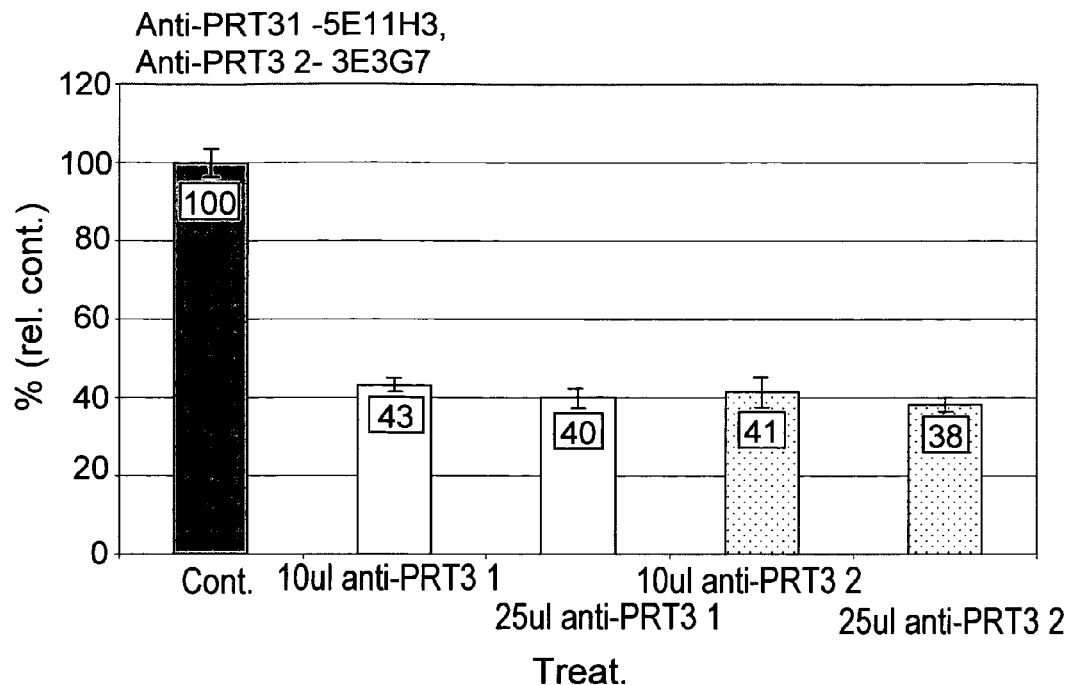

FIG. 6A-6C: Viability of human monocytes following 24-hour anti-KTPAF50 antibody treatment.

FIG. 6A: Histogram showing the effect of 24-hour treatment with anti-KTPAF50 antibody measured after 2-hour incubation with Resazurin.

FIG. 6B: Histogram showing the effect of 24-hour treatment with anti-KTPAF50 antibody measured after 4-hour incubation with Resazurin.

FIG. 6C: Histogram showing the effect of 24-hour treatment with anti-KTPAF50 antibody measured after 24-hour incubation with Resazurin.

Abbreviations: anti-PRT3 1=antibody 5E11H3; anti-PRT3 2=antibody 3E3G7; rel.=relative; cont.=control; treat.=treatment.

Figure 7A:
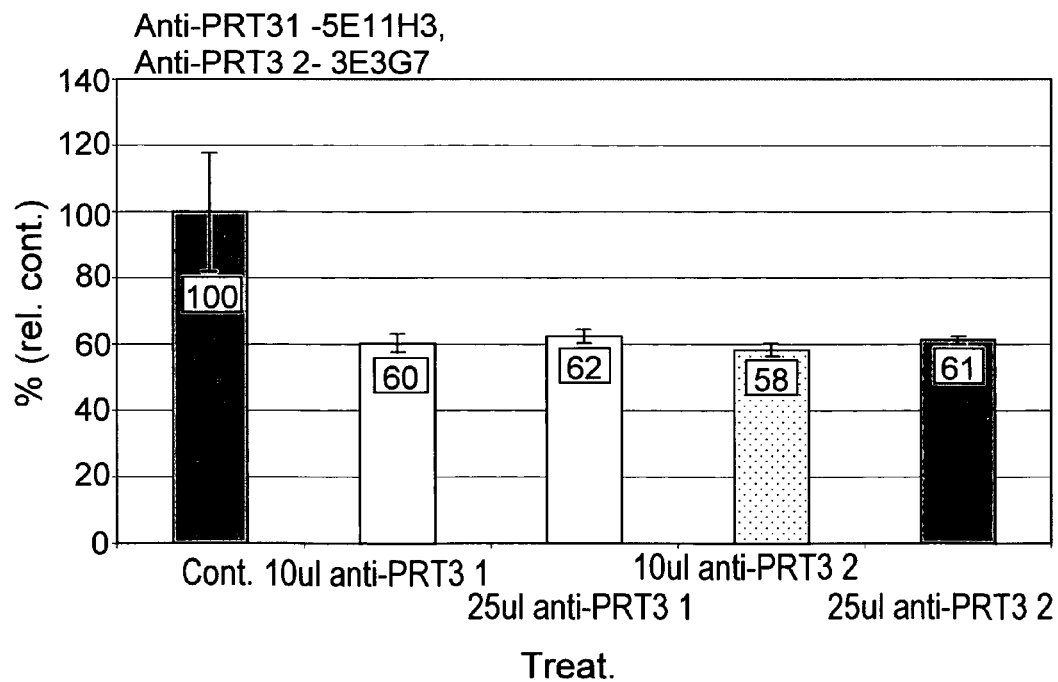
Figure 7B:
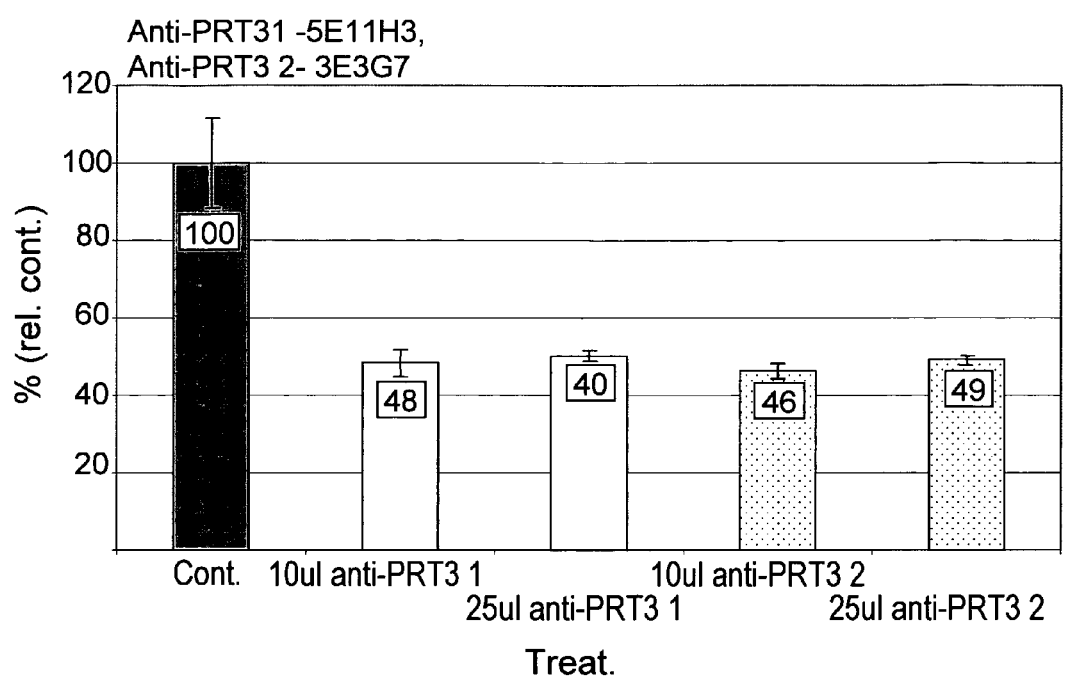

FIG. 7A-7B: Viability of human monocytes following 48-hour anti-KTPAF50 antibody treatment.

FIG. 7A: Histogram showing the effect of 48-hour treatment with anti-KTPAF50 antibody measured after 2-hour incubation with Resazurin.

FIG. 7B: Histogram showing the effect of 48-hour treatment with anti-KTPAF50 antibody measured after 4-hour incubation with Resazurin.

Abbreviations: anti-PRT3 1=antibody 5E11H3; anti-PRT3 2=antibody 3E3G7; rel.=relative; cont.=control; treat.=treatment.

FIG. 8A-8E: Effect KTPAF50 antibodies on TNF-α expression in human monocytes.

Figure 8A:
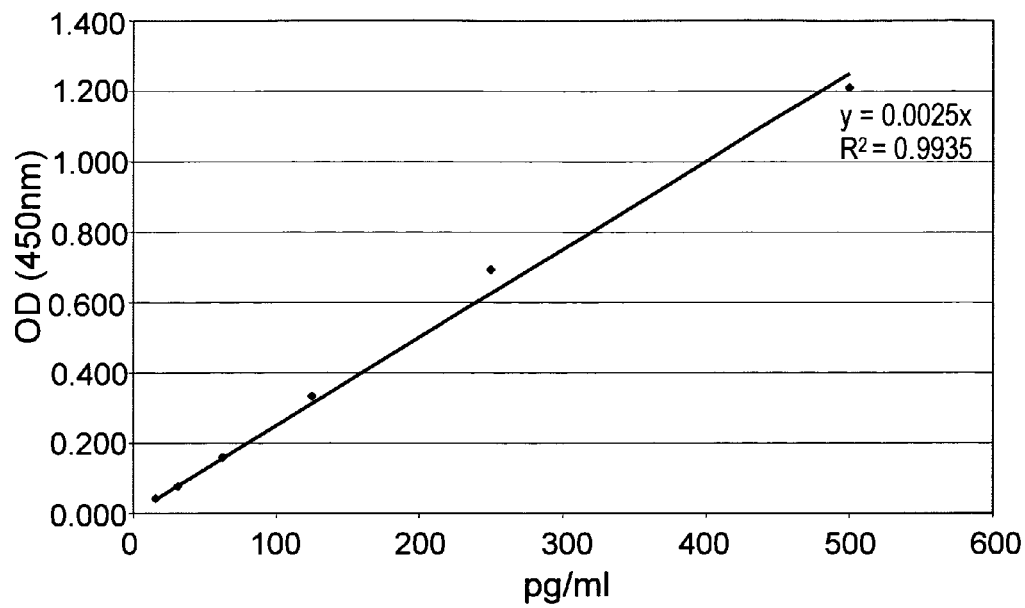

FIG. 8A: TNF-α calibration.

Figure 8B:
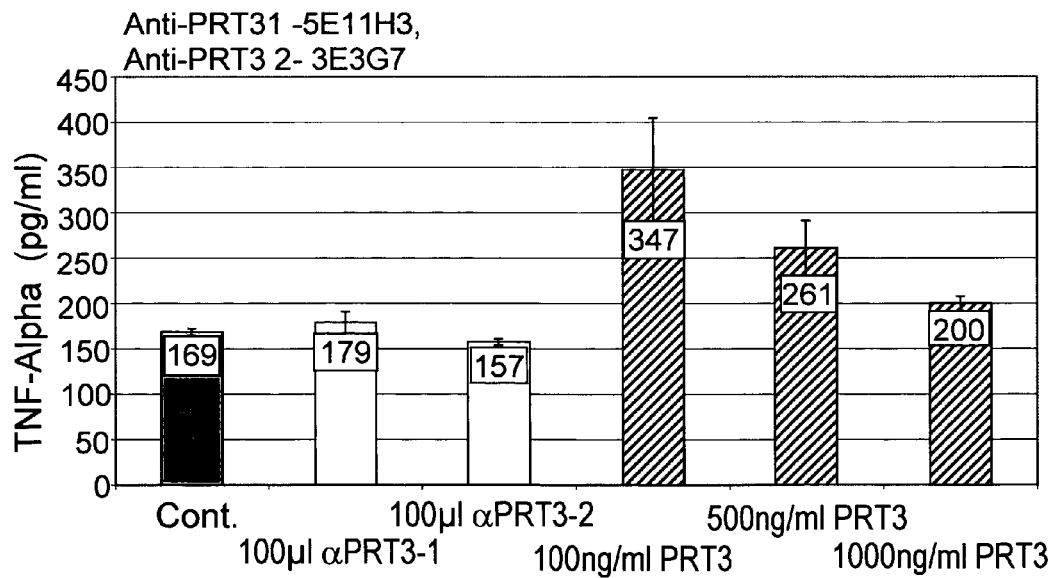

FIG. 8B: Histogram showing the effect of 24-hour treatment with KTPAF50 antibodies on TNF-α expression.

Figure 8C:
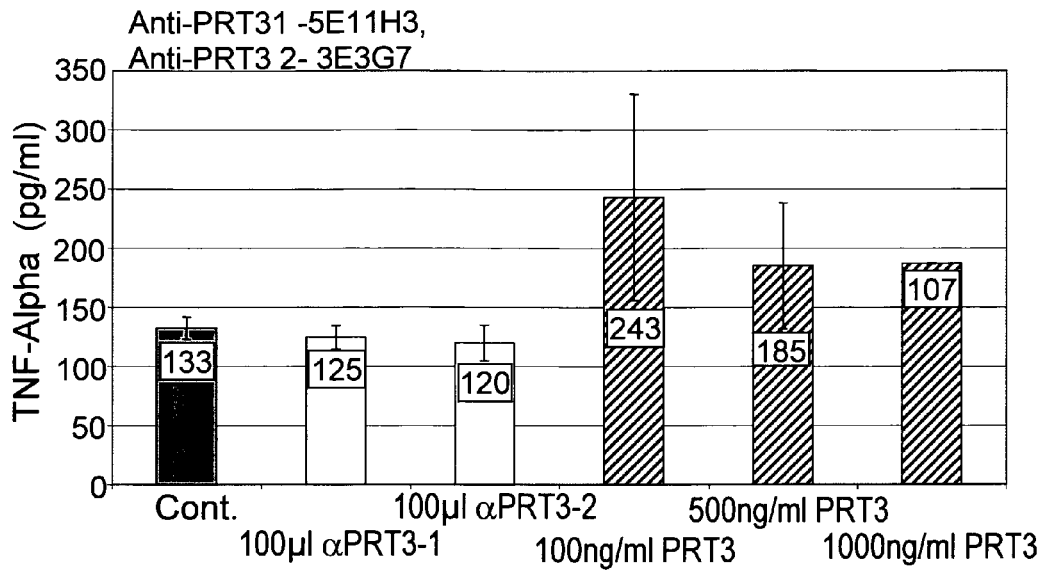

FIG. 8C: Histogram showing the effect of 48-hour treatment with KTPAF50 antibodies on TNF-α expression.

Figure 8D:
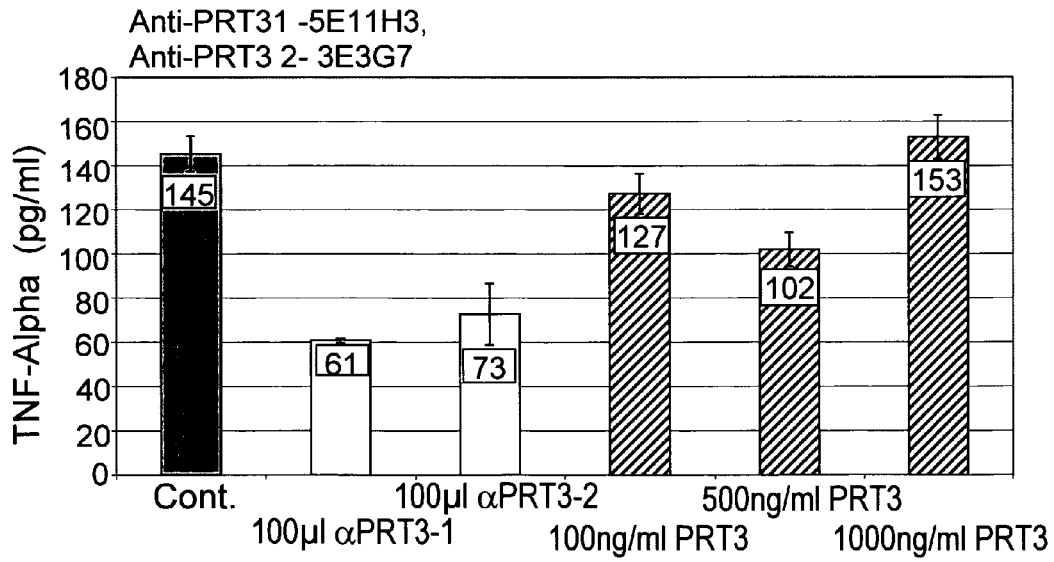

FIG. 8D: Histogram showing the effect of 120-hour treatment with KTPAF50 antibodies on TNF-α expression.

Figure 8E:
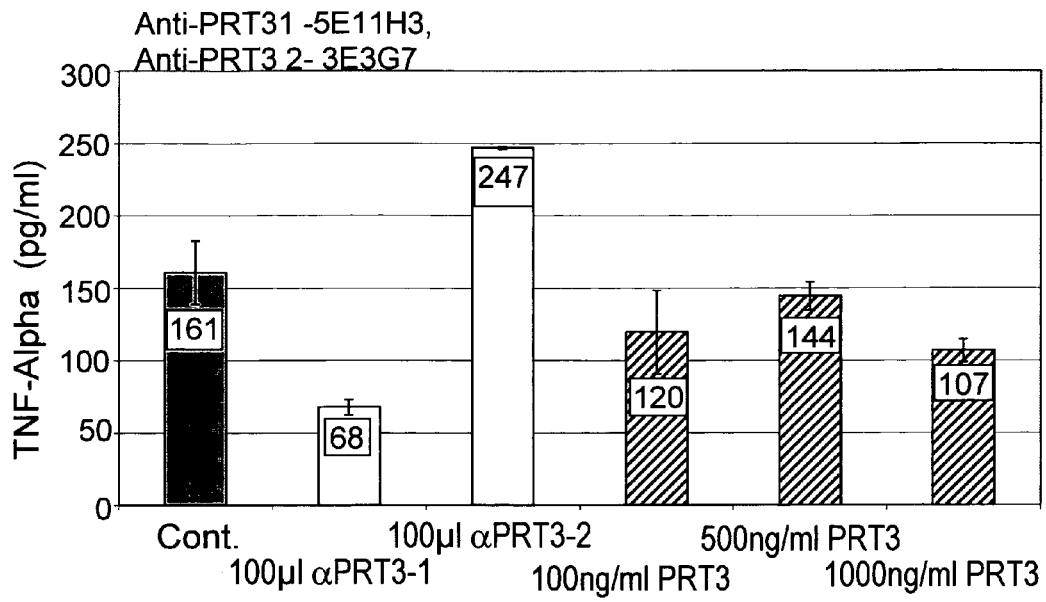

FIG. 8E: Histogram showing the effect of 144-hour treatment with KTPAF50 antibodies on TNF-α expression.

Abbreviations: anti-PRT3 1=5E11H3; anti-PRT3 2=3E3G7; cont.=control.

FIG. 9A-9E: Effect KTPAF50 antibodies on INF-γ expression in human monocytes.

Figure 9A:
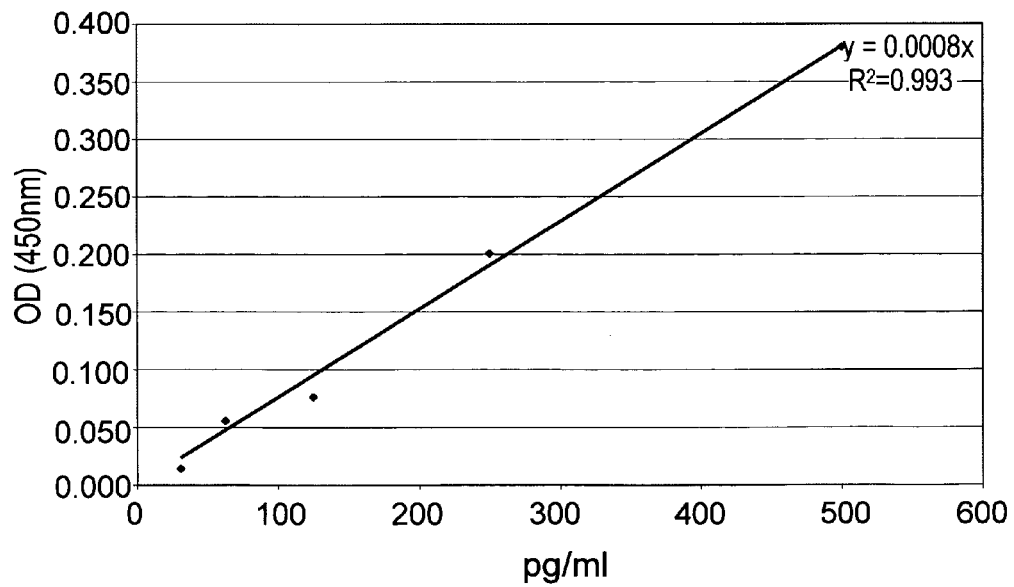

FIG. 9A: INF-γ calibration.

Figure 9B:
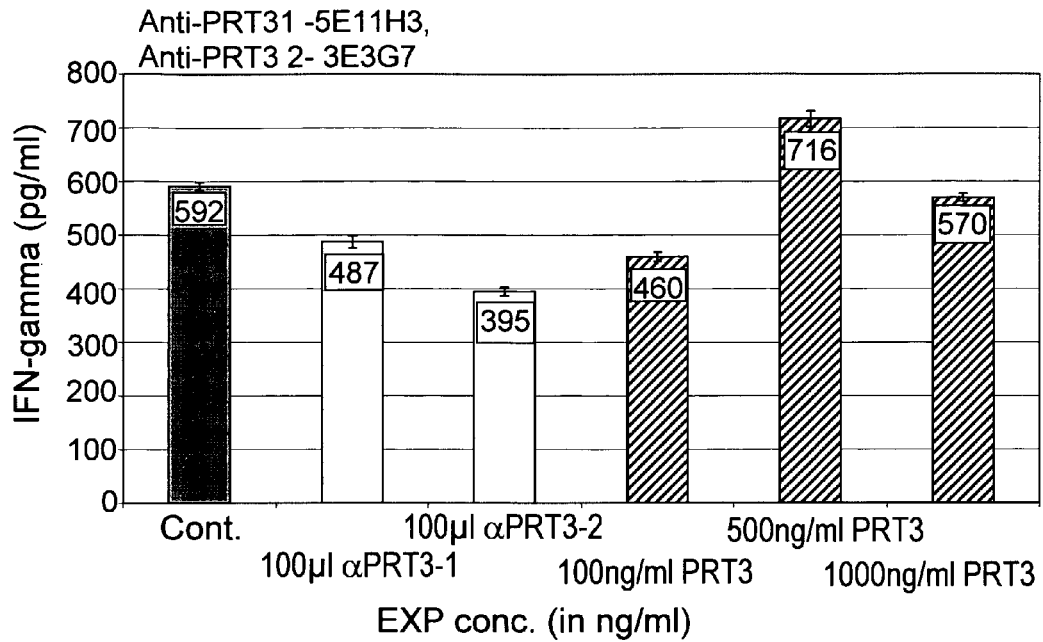

FIG. 9B: Histogram showing the effect of 24-hour treatment with KTPAF50 antibodies on INF-γ expression.

Figure 9C:
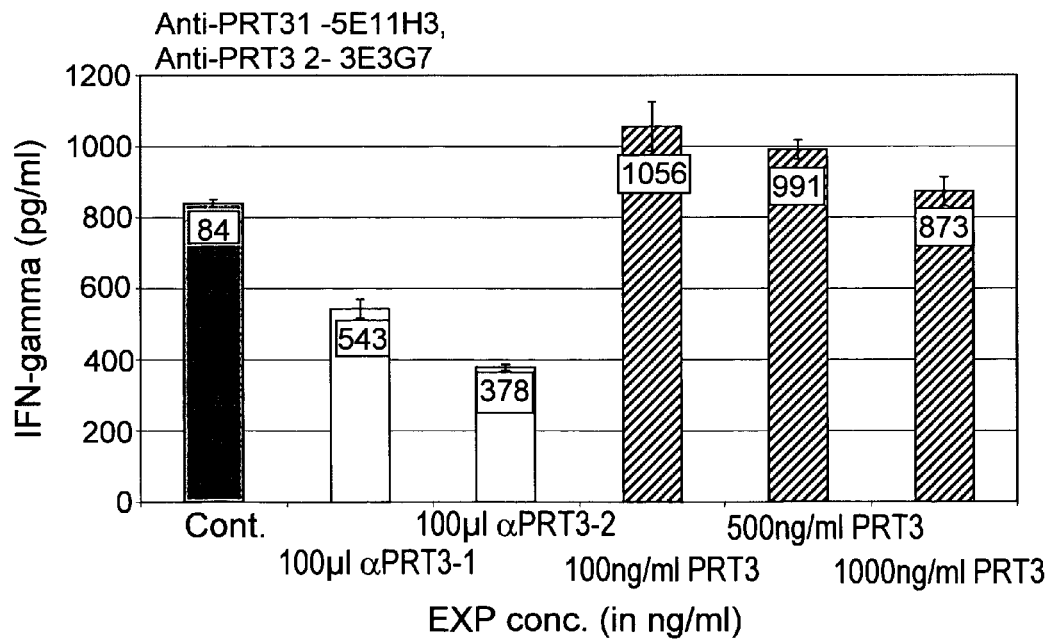

FIG. 9C: Histogram showing the effect of 48-hour treatment with KTPAF50 antibodies on INF-γ expression.

Figure 9D:
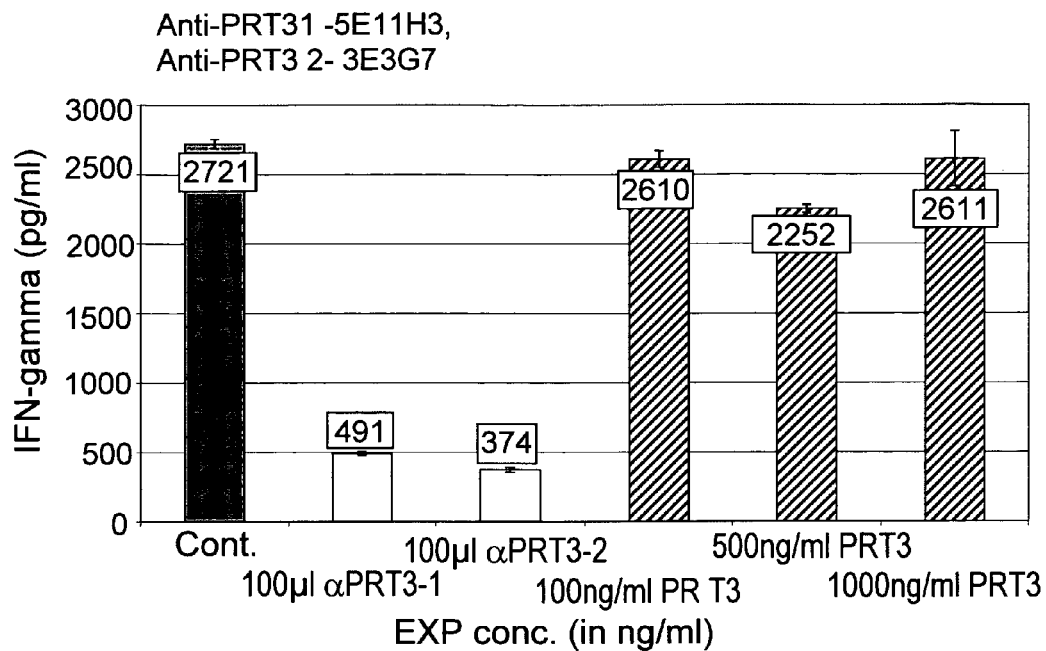

FIG. 9D: Histogram showing the effect of 120-hour treatment with KTPAF50 antibodies on INF-γ expression.

Figure 9E:
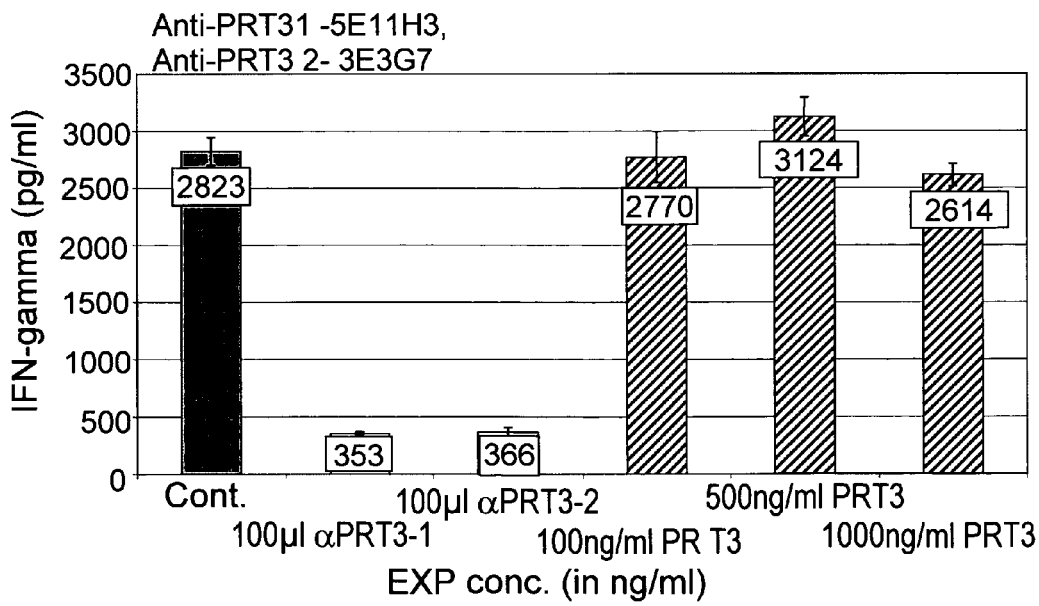

FIG. 9E: Histogram showing the effect of 144-hour treatment with KTPAF50 antibodies on INF-γ expression.

Abbreviations: anti-PRT3 1=5E11H3; anti-PRT3 2=3E3G7; conc.=concentration.

FIG. 10A-10D: Effect KTPAF50 antibodies on IL-10 expression in human monocytes.

Figure 10A:
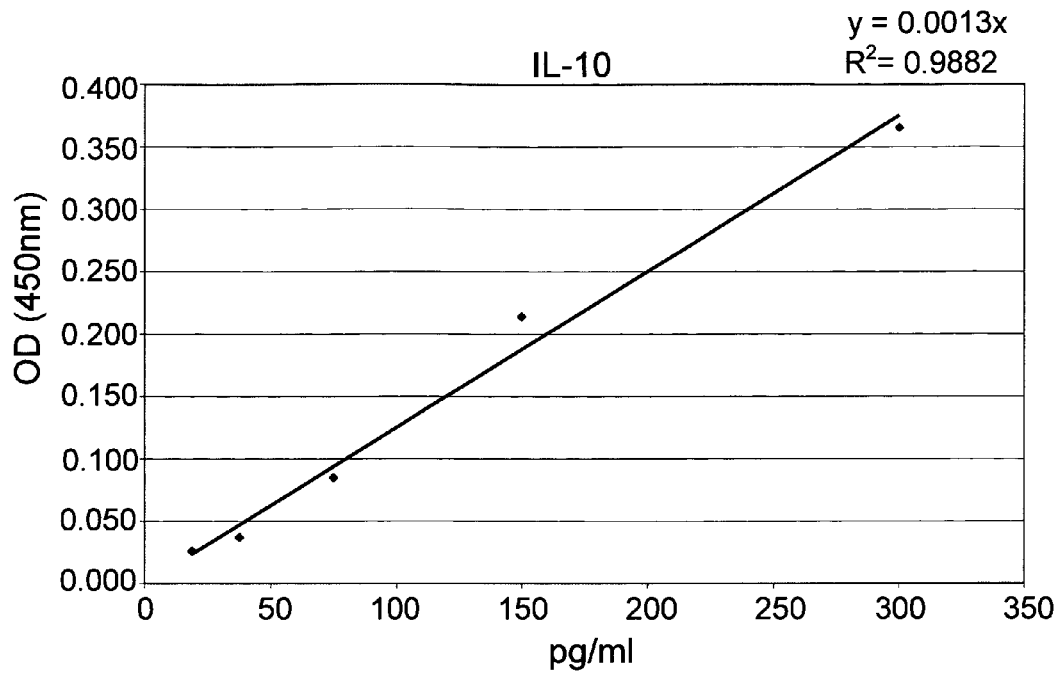

FIG. 10A: IL-10 calibration.

Figure 10B:
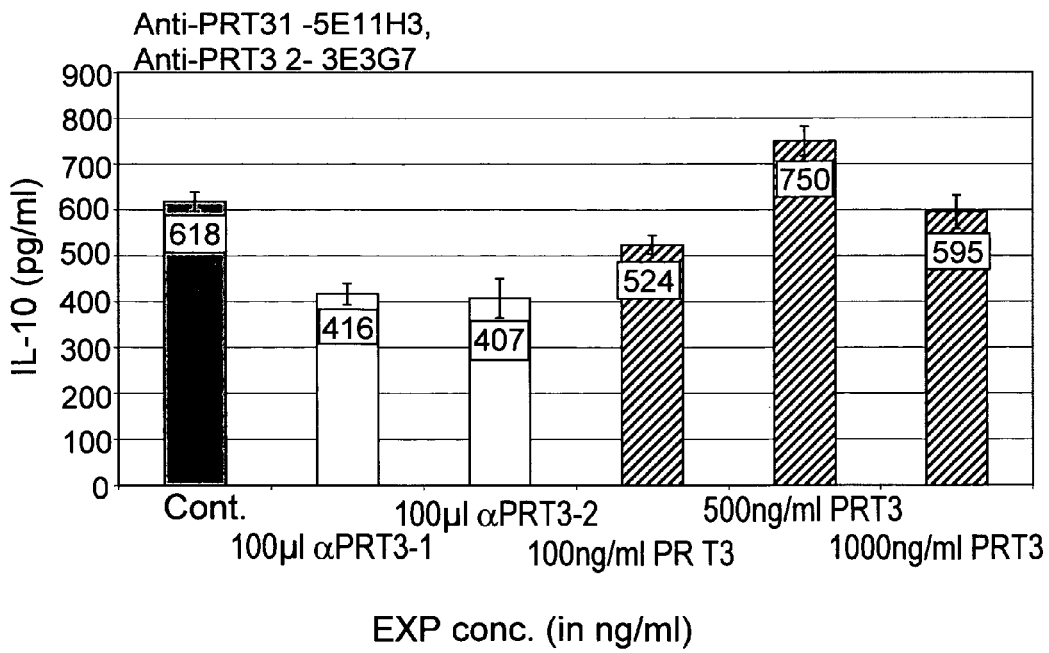

FIG. 10B: Histogram showing the effect of 24-hour treatment with KTPAF50 antibodies on IL-10 expression.

Figure 10C:
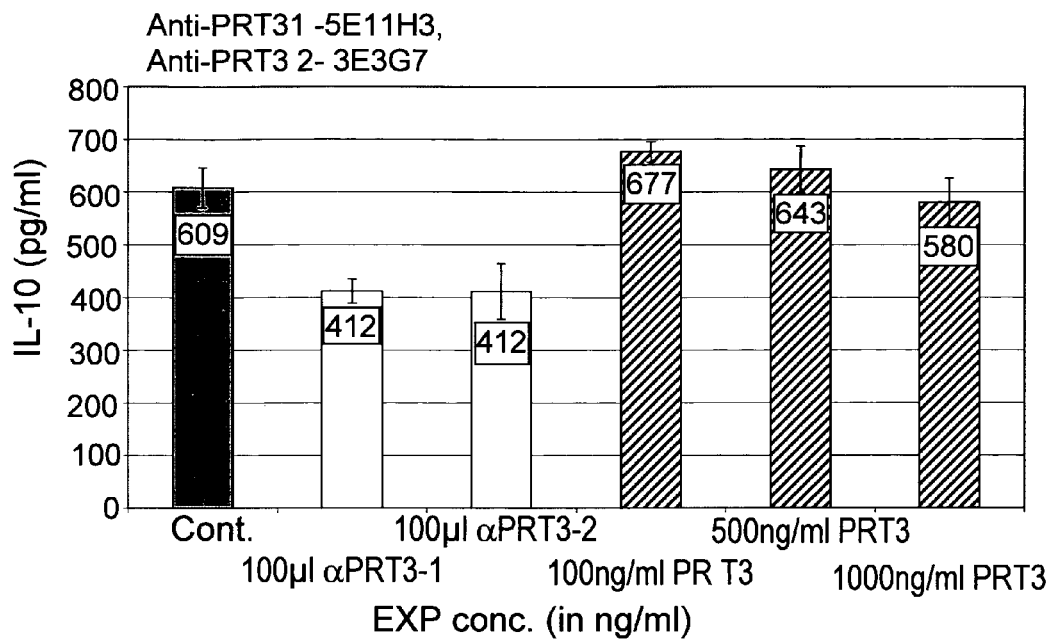

FIG. 10C: Histogram showing the effect of 48-hour treatment with KTPAF50 antibodies on IL-10 expression.

Figure 10D:
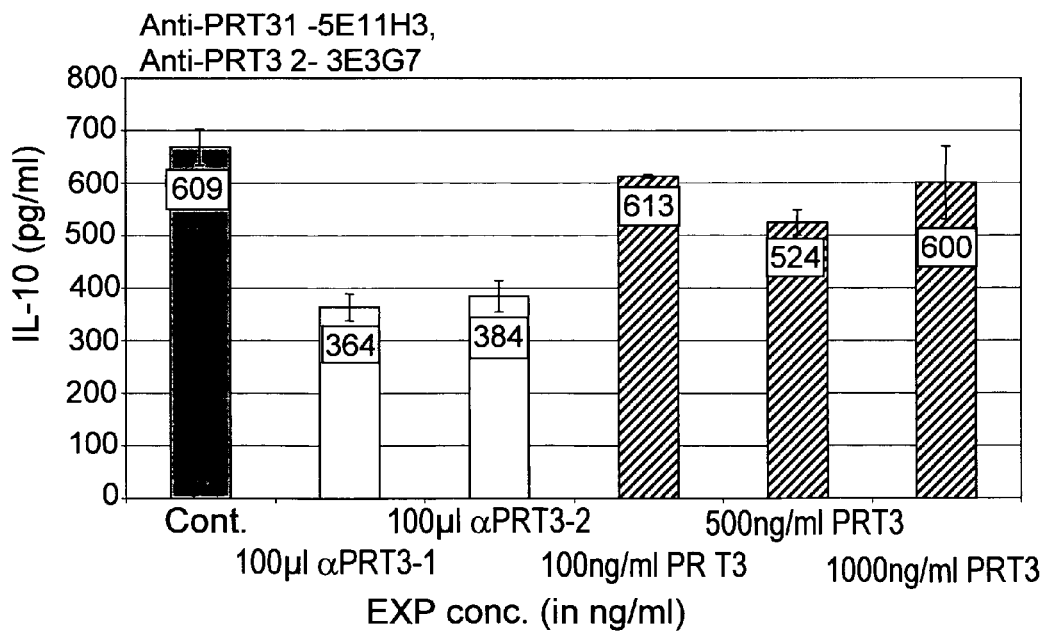

FIG. 10D: Histogram showing the effect of 120-hour treatment with KTPAF50 antibodies on IL-10 expression.

Figure 11:
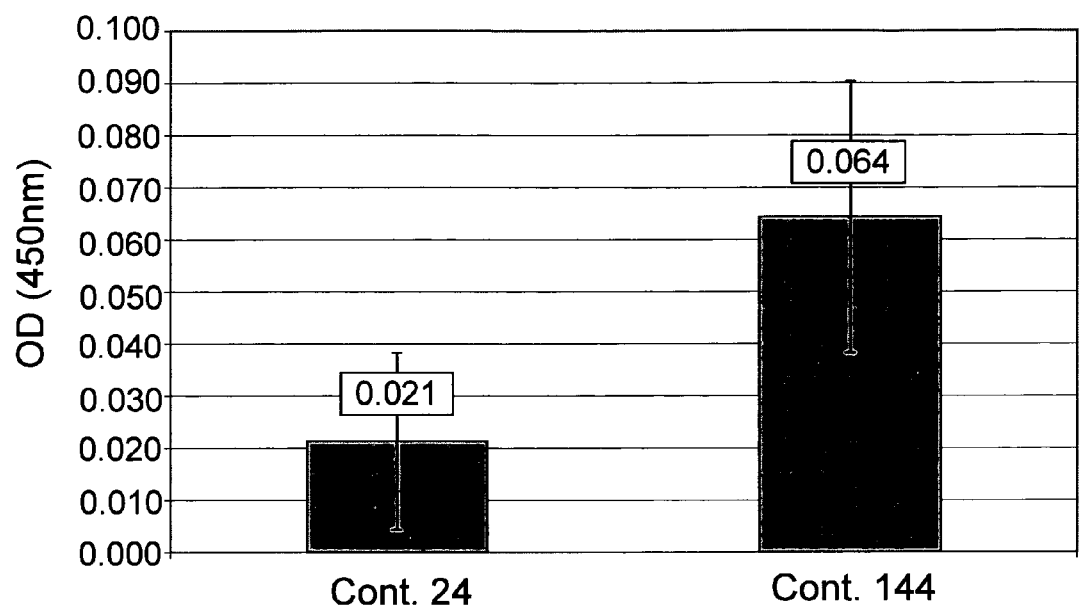

FIG. 11: Presence of KTPAF50 protein in the medium of human monocytes, following 24-hour and 144-hour incubation.

Abbreviation: cont.=control.

FIG. 12A-12F: Change in cell morphology following anti-KTPAF50 treatment visualized by light microscopy.

FIG. 12A: Control.

Figure 12A:
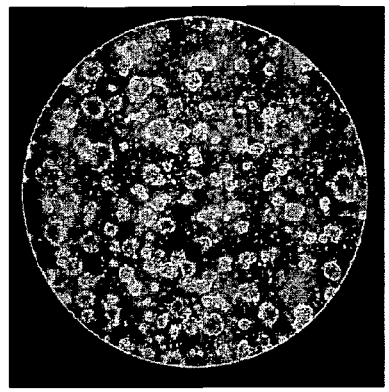
Figure 12B:
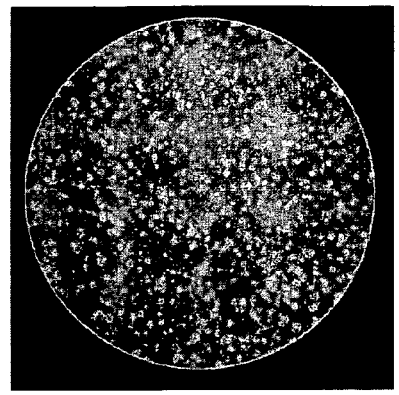

FIG. 12B: Cells treated with 100 µl of anti-KTPAF50 antibody (α-PRT3 1).

Figure 12C:
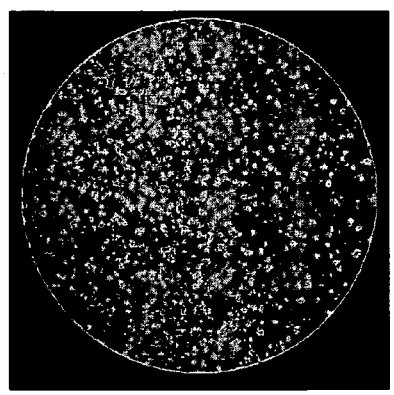

FIG. 12C: Cells treated with 1000 of anti-KTPAF50 antibody (α-PRT3 2).

Figure 12D:
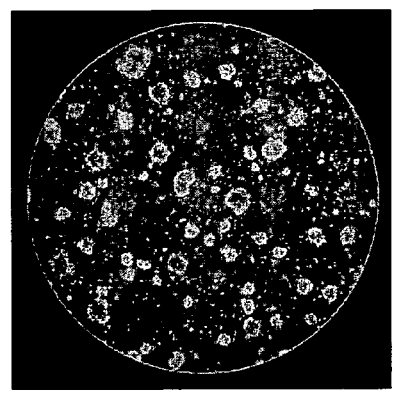

FIG. 12D: Cells treated with 100 ng/ml of KTPAF50 protein.

Figure 12E:
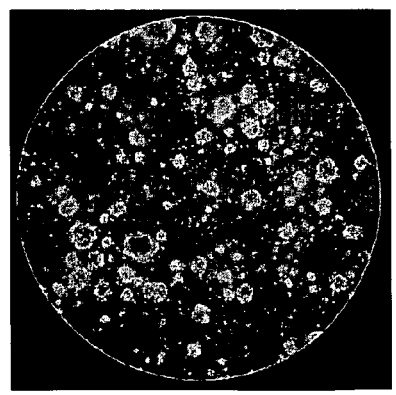

FIG. 12E: Cells treated with 500 ng/ml of KTPAF50 protein.

Figure 12F:
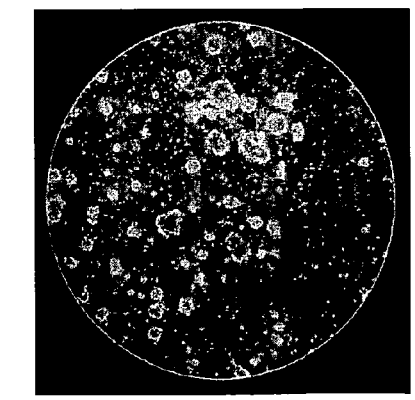

FIG. 12F: Cells treated with 1000 ng/ml of KTPAF50 protein.

DETAILED DESCRIPTION OF THE INVENTION

In previous reports, the inventors described a protein, denominated KTPAF50 (also referred to herein as PRT3), providing its expression patterns and biological activity [WO 2009/083968]. For the purposes of the present invention, the contents of WO 2009/083968 are fully incorporated herein by reference.

Most notably, WO 2009/083968 describes KTPAF50 expression patterns. Furthermore, WO 2009/083968 provides the sequence of KTPAF50 full-length protein without the signal peptide, provided herein as SEQ. ID. NO.1, as well as the sequence of KTPAF50 full-length protein with the signal peptide, provided herein as SEQ. ID. NO.2. In addition, an N-terminal peptide, 36 amino acids long, is also described in WO 2009/083968, which is herein depicted as SEQ. ID. NO.4.

In the present invention, the inventors describe the development of antibodies that recognize and bind KTPAF50 protein and/or KTPAF50-derived peptides.

Surprisingly, as described in Example 1 below, said antibodies were shown to be specific in the identification of said proteins in certain types of cancer, particularly lung, which did not directly correlate with KTPAF50's tissue expression as described in WO 2009/083968.

The inventors also demonstrate that KTPAF50-specific antibodies are potent regulators of cell viability, and thus can be used as an important tool in regulating cell growth.

Unexpectedly, KTPAF50-specific antibodies are shown herein as effective regulators of pro-inflammatory cytokine expression. These results suggest KTPAF50's pivotal role in the homeostatic balance of the immune system, and providing the antibodies as potential immunoregulators.

Thus, in a first aspect, the present invention provides an antibody which specifically recognizes the KTPAF50 protein or any fragments or derivatives thereof. Specifically, said KTPAF50 protein is denoted by SEQ ID NO. 1 or SEQ. ID. NO. 2. SEQ. ID. NO. 1 is 50 aa long, and relates to the KTPAF50 protein without the signal peptide. SEQ. ID. NO.2 is 74 aa long, and relates to the full length KTPAF50 protein, including the signal peptide, as previously described in WO 2009/083968.

As defined herein, the antibodies of the invention are usually naturally derived, or naturally produced. Thus, the antibodies are polyclonal antibodies or monoclonal antibodies. Alternatively, the antibodies of the invention may be synthetically produced by e.g. chemical synthesis, or recombinantly produced through the isolation of the specific mRNA from the respective antibody-producing cell or cell line. Said specific mRNA shall then undergo standard molecular biology manipulations (obtaining cDNA, introducing said cDNA into expression vectors, etc.) in order to generate a recombinantly produced antibody. Said techniques are well known to the man skilled in the art.

The generation of polyclonal antibodies against proteins is a technique well known to the man skilled in the art, and it is described, inter alia, in Chapter 2 of Current Protocols in Immunology, John E. Coligan et al. (eds.), Wiley and Sons Inc.

Monoclonal antibodies may be prepared from B cells taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology. Spleen or lymph node cells of these animals may be used in the same way as spleen or lymph node cells of protein-immunized animals, for the generation of monoclonal antibodies as described in Chapter 2 therein. The techniques used in generating monoclonal antibodies are further described by Kohler and Milstein [Kohler and Milstein (1975) Nature 256; 495-497], and in U.S. Pat. No. 4,376,110.

Example 2 below describes the 30 KTPAF50-specific monoclonal antibodies generated by the present inventors. Table 2 presents the antigenic specificity of each antibody and Table 3 shows their antigenic affinity.

The term "antibody" is also meant to include both intact molecules as well as fragments thereof, such as, for example, scFv, Fv, Fab', Fab, diabody, linear antibody, F(ab')$_2$ antigen binding fragment of an antibody which are capable of binding antigen [Wahl et al. (1983) *J. Nucl. Med.* 24, 316-325].

Fab and F(ab')$_2$ and other fragments of the antibodies are useful in the detection of the proteins used as antigens for the generation of the antibodies of the invention, in biological samples, according to the methods disclosed herein for intact antibody molecules, as well as for the other uses of the antibodies disclosed herein. Such fragments can be produced for example by proteolytic cleavage, using enzymes such as papain (to produce Fab fragments) or pepsin (to produce F(ab')$_2$ fragments). Thus, the Fab and F(ab')$_2$ and other fragments of the antibodies useful in the present invention may be tagged with various tags, according to the intended use. These tags may be detectable tags, to facilitate detection, or toxic tags, which would kill tumor cells, or "inducing" tags, which may induce other cells or substances to kill tumor cells.

An antibody is said to be "capable of binding", or "recognizing" a molecule if it is capable of specifically reacting with the molecule (the antigen) and thereby the antibody binds to said molecule. The term "epitope" is meant to refer to the portion of any molecule capable of being bound by an antibody, which can also be recognized by that antibody or the cells producing that antibody. Epitopes or "antigenic determinants" usually consist of chemically active surface groupings of molecules such as amino acids or sugar side chains, and have specific three-dimensional structural characteristics as well as specific charge characteristics.

An "antigen" is a molecule or a portion of a molecule capable of being recognized and bound by an antibody. An antigen may have one or more than one epitope. The specific reaction referred to above is meant to indicate that the antigen will react, in a highly selective and specific manner, with its corresponding antibody and not with the multitude of other antibodies which may be evoked by other antigens.

The antibodies provided by the present invention may be of any isotype, IgG, IgM, IgE, IgA or IgD, particularly for the polyclonal antibodies.

The monoclonal antibodies may also be of any isotype.

The monoclonal antibodies provided herein and presented in Table 2, were usually IgG isotype.

In the present invention, the antigens used to generate the KTAPF50-specific antibodies of the invention correspond to the full length protein, or to peptides derived from the KTAPF50 protein.

The term "peptide" is used herein to denote a peptide, polypeptide or protein. The peptide may be obtained synthetically, through genetic engineering methods, expression in a host cell, or through any other suitable means. Unless indicated otherwise, a peptide is generally composed of naturally-occurring L-amino acids.

The term "biological characteristics", with respect to a peptide molecule, refers to the peptide's ability to exert at least one of the in vitro or in vivo effects that may be exerted by the full KTPAF50 peptide or the KTPAF50 peptide, including but not limited to the biological activities described in the specification. For example, biological characteristics include the ability to treat cancer, immune system associated diseases, viral diseases and inflammatory-based diseases.

Figure 1:
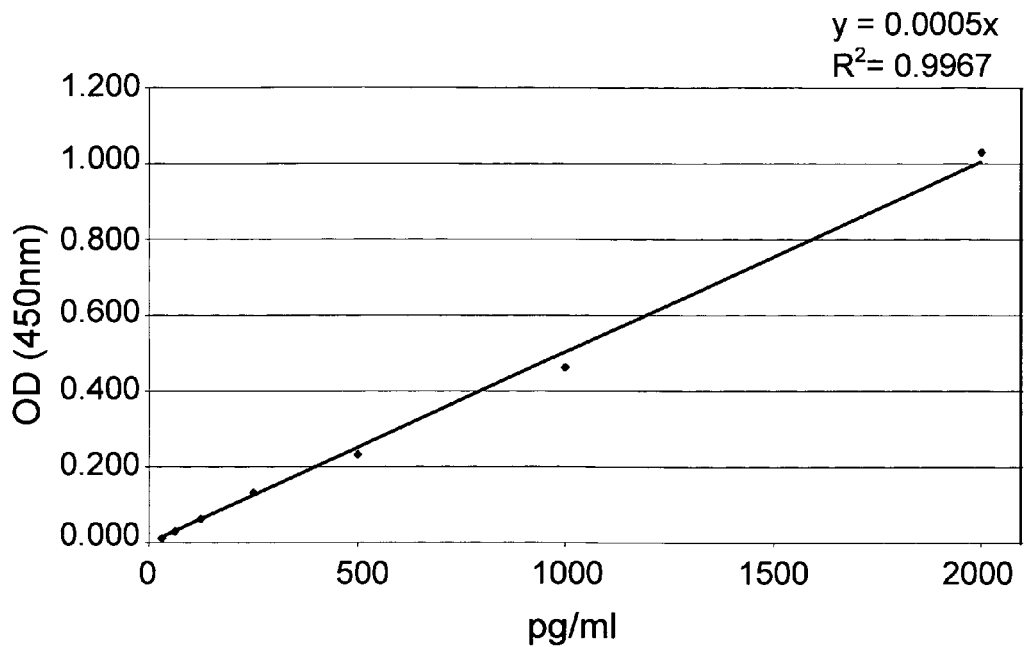
FIG. 1: Calibration curve showing the specificity of anti-KTPAF50 to the KTPAF50 antigen.

With regard to the antibodies, "biological characteristics" or "biological activity" usually refers to the antibodies' ability to specifically recognize the epitope, and consequently bind to it. The epitope may be part of the full-length protein or may be embedded in a fragment of the protein or in a peptide. As demonstrated in the Examples and exemplified in the Figures, FIG. 1 showed the specificity of the anti-KTPAF50 antibody to the KTPAF50 protein. Similarly on FIG. 3, the specificity of the anti-T101 antibody is shown with respect to the T101 protein.

The term "without significantly affecting the biological characteristics of the modified molecule as compared to the unmodified molecule" means to denote that the modified molecule retains a biological activity qualitatively similar to that of the unmodified molecule.

With respect to a modified peptide, in connection with the present invention, this means that it retains one or more of the biological characteristics of a protein of SEQ. ID. NO. 1, SEQ. ID. NO. 2, SEQ. ID. NO. 3, SEQ. ID. NO. 5, SEQ. ID. NO. 6, SEQ. ID. NO. 7. In order to determine whether a peptide retains a biological activity qualitatively similar to that of the unmodified molecule, one or more assays can be carried out, such as for example an in vitro, in vivo or a clinical experiment in which a modified peptide is compared to the corresponding unmodified one (namely that of the full KTPAF50 peptide or a KTPAF50 peptide) that is assayed in parallel; or an experiment in which the modified peptide is assayed to examine whether it has a biological effect similar to that of the unmodified peptide as known from separately conducted experiment. Such an experiment may be carried out, for example, in a manner described in WO 2009/083968.

A modified peptide may be a peptide that includes a contiguous sequence of at least 8, 12, 15, 20, 25, 30, 35, 40 or at least 45 amino acid residues that has a degree of identity to a corresponding sequence of at least 8, 12, 15, 20, 25, 30, 35, 40 or at least 45 amino acid residues included in the KTPAF50 peptide, the degree of identity being at least 70%, preferably at least 80%, more preferably at least 90% and particularly at least 95%.

Also provided by the invention are antibodies that can recognize modified peptides derived from KTPAF50, e.g., modified peptides in which one or more amino acids are replaced by another amino acid by conservative substitution. As used herein, "conservative substitution" refers to the substitution of an amino acid in one class by an amino acid of the same class, where a class is defined by common physico-chemical amino acid side chain properties and high substitution frequencies in homologous proteins found in nature. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu is a conservative substitution.

In one embodiment, only one substitution is made in the amino acid sequence.

In another embodiment, two substitutions are made. In a further embodiment, three substitutions are made. The maximum number of substitutions should not exceed the number of amino acids which leaves at least 70%, desirably at least 80%, preferably at least 90%, most preferably at least 95% of the amino acids in the unsubstituted sequence. By one particular embodiment, the substitutions which include up to 3, at times up to 6 amino acid residues substituted by others, are conservative substitutions.

In a further embodiment, one or more amino acids may be replaced by D-amino acids, preferably the corresponding D-amino acids. In a particular embodiment, all of the amino acids are D-amino acids.

Thus, it is to be understood that the invention pertains to antibodies capable of recognizing a protein, polypeptide or peptide comprising a sequence structurally similar to the sequences disclosed herein (SEQ. ID. NO.1, SEQ. ID. NO. 2, SEQ. ID. NO.3, SEQ. ID. NO.5, SEQ. ID. NO.6, SEQ. ID. NO.7) with substantially equal or greater activity. Changes in the structure of the protein, polypeptide or peptide comprise one or more deletions, additions, or substitutions. The number of deletions or additions, which may occur at any point in the sequence, will generally be less than 25%, preferably less than 10% of the total amino acid number.

Preferred substitutions are changes that would not be expected to alter the secondary structure of the protein, polypeptide or peptide, i.e., conservative changes. The following list shows amino acids (right side) that may be exchanged for the original amino acids (left side).

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |

-continued

| Original Residue | Exemplary Substitution |
| --- | --- |
| Ser | Thr |
| Thr | Ser |
| Trp | Tyr |
| Tyr | Trp; Phe |
| Val | Ile; Leu |

Amino acids can also be grouped according to their essential features, such as charge, size of the side chain, and the like. The following list shows groups of similar amino acids. Preferred substitutions would exchange an amino acid present in one group with an amino acid from the same group, as follows:
1. Small aliphatic, nonpolar: Ala, Ser, Thr, Pro, Gly;
2. Polar negatively charged residues and their amides: Asp, Asn, Glu, Gln;
3. Polar positively charged residues: His, Arg, Lys;
4. Large aliphatic nonpolar residues: Met, Leu, Ile, Val, Cys;
5. Large aromatic residues: Phe, Tyr, Trp.

Further comments on amino acid substitutions and protein structure may be found in Schulz et al., Principles of Protein Structure, Springer-Verlag, New York, N.Y., 1979, and Creighton, T. E., Proteins: Structure and Molecular Properties, W.H. Freeman & Co., San Francisco, Calif. 1983.

The preferred conservative amino acid substitutions as detailed above are expected to substantially maintain or increase the function or activity of the protein recognized by the antibodies of the invention, as detailed herein below. Of course, any amino acid substitutions, additions, or deletions are considered to be within the scope of the invention where the resulting protein, polypeptide or peptide is an antigen recognized by the antibodies of the invention, i.e., an antigen which is substantially equal or superior in terms of function to the proteins recognized by the antibodies of the invention.

The protein recognized by the antibodies of the invention can be produced by conventional chemical methods, such as solid phase synthesis (using e.g. FMOC and BOC techniques), and solution phase synthesis. These proteins, polypeptides or peptides may also be produced in bacterial or insect cells or other eukaryotic transcriptional in vivo system, as detailed in the below-noted Current Protocols in Molecular Biology, Chapter 16. Following production, the protein, polypeptide or peptide are purified from the cells in which they have been produced. Peptide purification methods are known to the person of skill in the art and are detailed e.g., in Ausubel et al. (eds.) Current Protocols in Molecular Biology, Chapter 16, John Wiley and Sons, 2006 and in Coligan et al. (eds.). Current Protocols in Protein Science, Chapters 5 and 6, John Wiley and Sons, 2006. Advantageously, the protein, polypeptide or peptide may be produced as a fusion with a second protein, such as Glutathione-S-transferase (GST) or the like, or a sequence tag, such as the Histidine tag (His-tag) sequence. The use of fusion or tagged proteins simplifies the purification procedure, as detailed in the above-noted Current Protocols in Molecular Biology, Chapter 16, and in the instructions for the His-tag protein expression and purification kit [available, e.g. from Qiagen GmbH, Germany].

The proteins recognized by the antibodies of the invention can also be synthesized in cell-free systems, using, for example, cell extracts or ribosomes.

The antigens of the invention may be further modified to improve their function, affinity, or stability. For instance, cyclization may be used to impart greater stability and/or overall improved performance upon a peptide. A number of different cyclization methods have been developed, including side chain cyclization and backbone cyclization. These methods are well documented in the prior art [e.g. Yu et al., Bioorg. Med. Chem. 7, 161-75, 1999, Patel et al., J. Pept. Res. 53, 68-74, 1999, Valero et al., J. Pept. Res. 53, 56-67, 1999, Romanovskis et al., J. Pept. Res. 52, 356-74, 1998, Crozet et al. Mol. Divers. 3, 261-76, 1998, Rivier et al., J. Med. Chem. 41, 5012-9, 1998, Panzone et al., J. Antibiot. (Tokyo), 51, 872-9, 1998, Giblin et al., Proc. Natl. Acad. Sci. USA 95, 12814-8, 1998, Limal et al., J. Pept. Res. 52:121-9, 1998, and U.S. Pat. No. 5,444,150].

A particular method of cyclization involves stabilization of an amphipathic alpha-helix by using para-substituted amino acid derivatives of a benzene ring [Yu et al. (1999) id ibid]. Another particular method of cyclization is backbone cyclization, as disclosed in Reissmann et al., Biomed. Pept. Proteins Nucleic Acids 1:51-6, 1994-95, and in references therein. Another method of cyclization which involves backbone-to side chain connections may also be used [Reissmann et al. (1994-95) id ibid].

Nonetheless, according to the invention, the proteins recognized by the antibodies of the invention may be extended at the N-terminus and/or C-terminus thereof with various identical or different organic moieties which are not naturally occurring or synthetic amino acids. As an example for such extension, the protein, polypeptide or peptide may be extended at the N-terminus and/or C-terminus thereof with an N-acetyl group.

In order to improve peptide structure, the protein recognized by the antibodies of the invention can be coupled through their N-terminus to a lauryl-cysteine (LC) residue and/or through their C-terminus to a cysteine (C) residue, or to other residue/s suitable for linking the peptide to adjuvant/s for immunization.

In a further aspect, the present invention provides a composition comprising as active ingredient at least one antibody as described in the invention. Thus, said antibody comprised as the active agent of the composition of the invention is an antibody or a fragment thereof that recognizes and binds KTPAF50, or any fragments, analogs or derivatives thereof.

Said composition may comprise a combination of monoclonal antibodies from different hydridomas. For example, said composition may comprise antibodies from two, three, four, five, or more hybridoma cell lines, according to the hybridomas described in Table 2.

In one embodiment, said composition is for use in diagnostic methods.

Said antibody or said composition comprising thereof are useful for the diagnosis of cancer and autoimmune disorders.

In particular, said antibody or said composition comprising thereof may be used in the diagnosis of lung cancer or IBD.

In another embodiment, said composition comprising at least one of the antibodies as described in the invention may be used in the treatment of cancer.

In a further embodiment, the composition comprising at least one of the antibodies as described in the invention may be used in the prognosis of cancer. A particularly need for prognosis exists in patients undergoing cancer treatment, in which it is essential to have indicators for treatment efficacy. Therefore, a composition comprising at least one antibody as described in the invention should be capable to determine, through the detection or the determination of the levels of KTPAF50, the outcome of the treatment.

The preparation of compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Compositions of the invention may further comprise at least one of pharmaceutically acceptable adjuvant, carrier, diluent or excipient.

By the term "pharmaceutically acceptable carrier" it is meant any one of inert, non-toxic materials, which do not react with the active ingredient. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemico-physical considerations, such as solubility and lack of reactivity with the antibodies of the invention, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way. Typical examples of carriers include (a) liquid solutions, where an effective amount of the active substance is dissolved in diluents, such as water, saline, natural juices, alcohols, syrups, etc.; (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of active agent as solids or granules; (c) powders; (d) suspensions in an appropriate liquid; (e) suitable emulsions; (f) liposome formulation; and others.

In another embodiment, compositions of the invention may also optionally further comprise additional active agents, such as, but not limited to antibiotics, cytokines, lymphokines, growth factors, hormones.

Also provided in the present invention are the antibody-producing cell lines, which produce an antibody according to the invention. Thus, the present invention provides hybridoma cell lines producing a monoclonal antibody against KTPAF50.

In one embodiment, the antibody-producing cells are clonally isolated and immortalized in order to produce the antibody-producing cell lines which are also the object of the present invention. Cell immortalization may be achieved as per the methods known to the man skilled in the art, and described, e.g., by Lanzavecchia et al., 2007 [Lanzavecchia A, Corti D, Sallusto F. (2007) Human monoclonal antibodies by immortalization of B cells. *Curr Opin Biotechnology;* 18(6):523-8].

Example 2 and Tables 2 and 3 below present all the hybridomas generated by the present inventors, the particular antigen used for their generation and their affinity for the antigen, as measured by ELISA.

Thus, the present invention also provides an antibody-producing cell line, or a hybridoma cell line.

In particular, the present invention provides the following hybridoma cell lines: 3E3G7, 5E11H3, 2B6A3, 2B6A12, 2B6G2, 2B6H1, 5E11B5, 5E11B8, 5E11H5, 3E1F9, 3E1F11, 3E1G4, 3E1G6, 2A8B8, 2A8B12, 2A8H7, 6E2B6, 6E2C5, 6E2C9, 6E2D4, 7D4D6, 7D4E12, 7D4F9, 7D4H10, 6F5A1, 6F5C9, 6F5C12, 3E3B3, and 3E3C8.

Two hybridoma cell lines (3E3G7 and 5E11H3) were deposited in the Collection Nationale de Culture de Microorganismes (CNCM), Institut Pasteur (25, Rue du Docteur Roux, F-75724, Paris, Cedex 15, France), a Depositary Institution according to the provisions of the Budapest Treaty, as follows:

| Hybridoma | Date of deposit | CNCM Reference Number | Registration Number |
|---|---|---|---|
| 5E11H3 | 24 Jun. 2010 | CNCM-28435.1006 | CNCM I-4331 |
| 3E3G7 | 28 Jun. 2010 | CNCM-28440.1006 | CNCM I-4335 |

The deposits are available as required by foreign patent laws in countries wherein counterparts of the subject application, or its progeny, are filed. However, it should be understood that the availability of the deposits does not constitute a license to practice the subject invention in derogation of patent rights granted by a governmental action.

Further, the subject hybridoma deposits were stored and made available to the public in accord with the provisions of the Budapest Treaty for the Deposit of Microorganisms, i.e., they were stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them Therefore, the present invention also provides the antibodies produced by said cell lines.

In another further aspect, the present invention provides the use of an antibody as described in the invention, which recognizes KTPAF50, in the preparation of a diagnostic composition. In particular, said composition is for the diagnosis of any one of cancer and autoimmune disease.

Thus, the present invention provides the use of the anti-KTPAF50 antibody in the preparation of a diagnostic composition for the diagnosis of cancer.

When referring herein to cancer it includes, but is not limited to, myeloid leukemia such as chronic myelogenous leukemia, acute myelogenous leukemia with maturation, acute promyelocytic leukemia, acute non-lymphocytic leukemia with increased basophiles, acute monocytic leukemia, acute myelomonocytic leukemia with eosinophilia, malignant lymphoma, such as Burkitt's non-Hodgkin's, lymphocytic leukemia, such as acute lymphoblastic leukemia, chronic lymphocytic leukemia, myeloproliferative diseases, solid tumors such as benign meningioma, mixed tumors of salivary gland, tumors in lip and oral cavity, pharynx, larynx, paranasal sinuses, colonic adenomas, adenocarcinomas, such as small cell lung cancer, kidney, uterus, prostate, bladder, ovary, colon, sarcomas, liposarcoma, myxoid, synovial sarcoma, rhabdomyosarcoma (alveolar), extraskeletal myxoid chondrosarcoma, Ewing's tumor, other include testicular and ovarian dysgerminoma, retinoblastoma, Wilms' tumor, neuroblastoma, malignant melanoma, mesothelioma, breast, skin, prostate, and ovarian cancer, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

Figure 2:
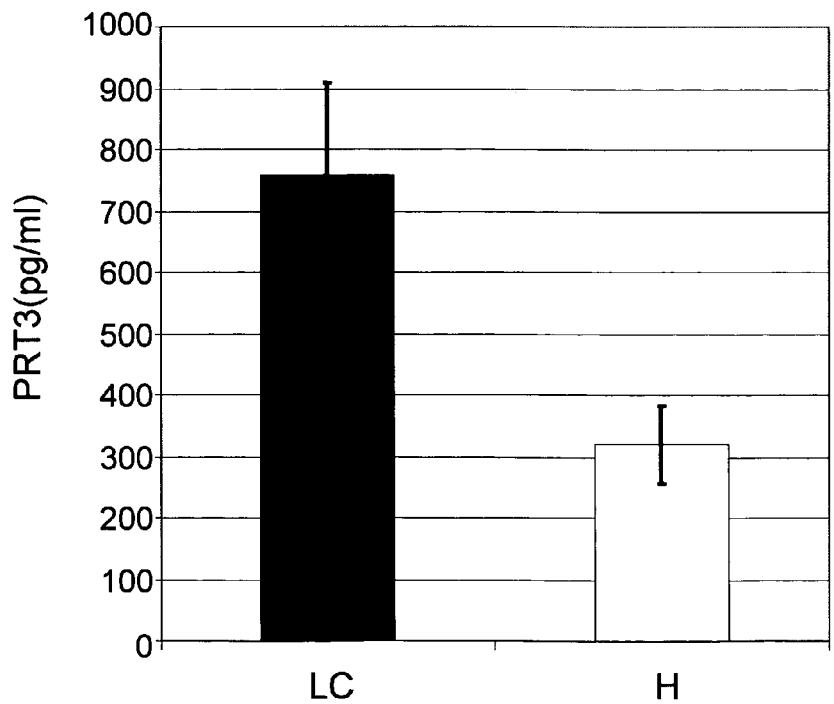
FIG. 2: Histogram showing KTPAF50 concentration in human blood serum obtained from patients with lung cancer (LC), compared with healthy individuals (H).

As demonstrated in the herein following Example 1 and in FIG. 2, KTPAF50 serum level was elevated in lung cancer and thus, the anti-KTPAF50 antibody showed valuable in the diagnosis of lung cancer.

The antibodies of the invention, or a composition comprising thereof, are also for use in the diagnosis of breast and ovarian cancer.

In addition, the present invention provides the use of the anti-KTPAF50 antibody in the preparation of a diagnostic composition for the diagnosis of an autoimmune disease.

As referred to herein, an autoimmune disease includes inflammatory bowel disease (IBD), Crohn's disease, multiple sclerosis (MS), autoimmune uveitis, autoimmune uveoretinitis, autoimmune thyroiditis, Hashimoto's disease, insulitis, Sjogren's syndrome, spontaneous abortions, experimental autoimmune myocarditis, rheumatoid arthritis (RA), lupus (SLE), psoriasis and diabetes, particularly type I. Additional examples of autoimmune diseases include Acute necrotizing hemorrhagic leukoencephalitis, Addison's disease, Agammaglobulinemia, Allergic asthma, Allergic rhinitis, Alopecia greata, Amyloidosis, Ankylosing spondylitis, Anti-GBM/Anti-TBM nephritis, Antiphospholipid syndrome (APS), Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune thrombocytopenic purpura (ATP), Axonal and neuronal neuropathies, Bal's disease, Behnet's disease, Bullous pemphigoid, Cardiomyopathy, Castleman disease, Celiac sprue (nontropical), Chagas' disease, Chronic fatigue syndrome, Chronic inflammatory demyelinating polyneuropathy (CIDP), Churg-Strauss syndrome, Cicatricial pemphigoid/benign mucosal pemphigoid, Cogan's syndrome, Cold agglutinin disease, Congenital heart block, Coxsackie myocarditis, CREST disease, Essential mixed cryoglobulinemia, Demyelinating neuropathies, Dermatomyositis, Devic disease, Discoid lupus, Dressler's syndrome, Endometriosis, Eosinophilic fasciitis, Erythema nodosum, Experimental allergic encephalomyelitis, Evan's syndrome, Fibromyalgia, Fibrosing alveolitis, Giant cell arteritis (temporal arteritis), Goodpasture's syndrome, Graves' disease, Guillain-Barre syndrome, Hemolytic anemia, Henoch-Schonlein purpura, Herpes gestationis, Hypogammaglobulinemia, Idiopathic thrombocytopenic purpura (ITP), IgA nephropathy, Immunoregulatory lipoproteins, Inclusion body myositis, Insulin-dependent diabetes (type1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lyme disease, Meniere's disease, Microscopic polyangiitis, Mixed connective tissue disease (MCTD), Mooren's ulcer, Mucha-Habermann disease, Myasthenia gravis, Myositis, Narcolepsy, Neutropenia, Ocular cicatricial pemphigoid, Osteoarthritis, Palindromic rheumatism, Paraneoplastic cerebellar degeneration, Paroxysmal nocturnal hemoglobinuria (PNH), Parsonnage-Turner syndrome, Pars planitis (peripheral uveitis), Pemphigus, Peripheral neuropathy, Perivenous. encephalomyelitis, Pernicious anemia, POEMS syndrome, Polyarteritis nodosa, Type I, II, and III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Psoriatic arthritis, Idiopathic pulmonary fibrosis, Pyoderma gangrenosum, Pure red cell aplasia, Raynaud's phenomenon, Reflex sympathetic dystrophy, Reiter's syndrome, Relapsing polychondritis, Restless legs syndrome, Rheumatic fever, Sarcoidosis, Schmidt syndrome, Scleritis, Scleroderma, Sperm and testicular autoimmunity, Stiff person syndrome, Subacute bacterial endocarditis (SBE), Sympathetic ophthalmia, Takayasu's arteritis, Temporal arteritis/Giant cell arteritis, Thrombocytopenic purpura (TTP), Autoimmune thyroid disease, Tolosa-Hunt syndrome, Transverse myelitis and necrotizing myelopathy, Ulcerative colitis, Undifferentiated connective tissue disease (UCTD), Vasculitis, Vesiculobullous dermatosis, Vitiligo and Wegener's granulomatosis.

In a further aspect, the present invention provides the use of an antibody as described in the invention, specific for KTPAF50, in the preparation of a therapeutic composition for the treatment of cancer, autoimmune diseases, graft rejection, neurodegenerative diseases and diabetes.

In particular said composition is for the treatment of cancer.

As shown in Example 3, treatment with KTPAF50-specific antibodies caused reduction of cell viability, suggesting that these antibodies may be used to induce cell death, or to induce apoptosis. Induction of cell death in cancerous cells can be an effective means for their elimination.

Thus, the present invention provides a method of treatment of cancer, said method comprising administering a therapeutically effective amount of at least one antibody of the invention, or a combination thereof, to a subject in need.

Further, the antibodies, or fragments thereof, provided in the present invention, may be used to quantitatively or qualitatively detect the proteins used as antigens for the generation of the antibodies of the invention, in a sample. This can be accomplished by techniques giving a visually detectable signal, which may be any one of fluorescence (immunofluorescence), a chromogenic product of an enzymatic reaction, production of a precipitate, chemiluminescence or bioluminescence. Employing a fluorescently or color-labeled antibody coupled with light microscopy, flow cytometry, or fluorometric detection as described below. Other techniques and labels which may be used for detecting the antibody include, but are not limited to colloidal gold, radioactive tag, GFP (green fluorescence protein), and the like, avidin/streptavidin-biotin, magnetic beads, as well as physical systems, e.g. nanotechnological system, sensitive to the actual binding.

The antibodies, or fragments thereof, provided in the present invention may be employed in histology staining, as in immunohistochemistry, immunofluorescence or immunoelectron microscopy, as well as for in situ detection of the proteins. In situ detection may be accomplished by removing a histological specimen from a subject, and contacting the labeled antibody of the present invention with such a specimen. The antibody (or fragment) is contacted by applying or by overlaying the labeled antibody (or fragment) to a biological sample (said specimen). Through the use of such a procedure, it is possible to determine not only the presence of the antigen, but also its distribution on the examined tissue. Using the present invention, those of ordinary skill will readily perceive that any of a wide variety of histological methods, such as staining procedures can be modified in order to achieve such in situ detection.

One of the ways in which an antibody in accordance with the present invention can be labeled and directly detected is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholine-esterase. The detection can be accomplished by colorimetric methods which employ a chromogenic substrate for the enzyme. Detection may also be accomplished by visual comparison of the extent of enzymatic reaction of a substrate with similarly prepared standards (this procedure is suitable for both soluble color products and non-soluble color products, e.g. on nitrocellulose or plastic supports).

In the present invention, detecting the reaction of the antibody with the antigen can be further aided, in appropriate instances, by the use of a secondary antibody or other ligand which is reactive with the ligand or reacted antibody, either specifically with a different epitope, or non-specifically Enzyme immunoassays such as immunofluorescence assays (IFA), photometric assays, enzyme linked immunoabsorbent assays (ELISA), ELISPOT assay, and immunoblotting can be readily adapted to accomplish the detection of the specific antibodies.

Other detection systems which may also be used include those based on the use of protein A derived from *Staphylococcus aureus* Cowan strain I, protein G from group C *Streptococcus* sp. (strain 26RP66), or systems which employ the use of the biotin-avidin binding reaction.

Other methods of immunoenzymatic detection in which the antibodies of the invention may be employed are the Western blot, and the dot blot. The sample is separated by electrophoresis and transferred to a nitrocellulose membrane or other suitable support. The sample to be tested (e.g. culture supernatant) is then brought into contact with the membrane and the presence of the immune complexes formed is detected by the method already described. In a variation on this method, purified antibodies are applied in lines or spots on a membrane and allowed to bind. The membrane is subsequently brought into contact with the sample before and after culture to be tested and the immune complexes formed are detected using the techniques described herein.

The presence of antibody-antigen complexes may also be detected by agglutination. The antibodies according to this invention, may be used to coat, for example, latex particles which form a uniform suspension. When mixed with a sample, e.g. serum containing specific antigens recognized by the antibodies, the latex particles are caused to agglutinate and the presence of large aggregates can be detected visually.

For a review of immunological and immunoassay procedures applicable to the measurement of antibodies by immunoassay techniques, see Basic and Clinical Immunology [D. Stites et al. (eds.) (1994) Basic and Clinical Immunology, 8$^{th}$ ed.].

Detecting the reaction of the antibody with the antigen can be facilitated by the use of an antibody or ligand that is labeled with a detectable moiety by methods known in the art. Such a detectable moiety allows visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase and alkaline phosphatase (for either light microscopy or electron microscopy and biochemical detection and for biochemical detection by color change), and biotin-streptavidin (for light or electron microscopy). The detection methods and moieties used can be selected, for example, from the list above or other suitable examples by the standard criteria applied to such selections [Harlow and Lane (1988) Antibodies: A Laboratory Manual, Cold Spring Harbor Laboratory, Cold Spring Harbor, N.Y.].

Detection may be accomplished using any of a variety of other immunoassays. For example, by radioactive labeling the antibodies or antibody fragments, it is possible to detect antigens through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a gamma/beta counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, phycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantification of the ternary complex formed between solid-phase antibody, antigen, and labeled antibody.

Antibodies of the invention may be radiolabeled in order to be used for imaging of a number of different cancers. Radioisotopes like In$^{111}$ and Tc$^{99}$ are used for labeling antibodies and visualization by imaging techniques. Radio-immunoscintigraphy (RIS) is a functional examination that allows for the in vivo imaging of tumors. This is accomplished using radiolabeled antibodies and standard gamma scintillation cameras.

Thus, the present invention is useful as a screening assay for the detection or indication of the presence of a tumor or cancer in a subject. The antibodies, or fragments thereof, when directly conjugated to a detectable marker as described herein, may be used in the detection of the antigen (or a fragment thereof) in vivo, indicating the presence of cancerous cells, and visualized with the help of imaging techniques, by injection into a subject to be diagnosed and detection by imaging.

Furthermore, the antibodies provided by the invention may be conjugated to cytotoxic drugs, in order to be used, either per se or as part of a composition, in the treatment of cancer.

Hence; as mentioned above, the antibodies provided by the invention are suitable as a delivery system for toxic drugs in order to kill cancerous, or pre-cancerous cells.

One example of a cytotoxic drug is an anti-proliferative drug molecule, which may be covalently coupled directly or via a linker to the antibody, and wherein said antibody may optionally be specifically cleavable by a protease abundant in or secreted by cancer cells, thereby preferentially releasing the anti-proliferative drug within, near or at the cancer cells by the action of the protease.

Examples of anti-proliferative drugs are cyclophosphamide, chlorambucil, busulfan, Melphalan, Thiotepa, ifosfamide, Nitrogen mustard, methotrexate, 5-Fluorouracil cytosine arabinoside, 6-thioguanine, 6-mercaptopurine, doxorubicin, daunorubicin, idorubicin, dactinomycin, bleomycin, mitomycin, plicamycin, epipodophyllotoxins vincristin, vinblastin, vinclestin, Etoposide, Teniposide, carmustin, lomustin, semustin, streptozocin, adrenocorticoids, estrogens, antiestrogens, progestins, aromatase inhibitors, androgens, anti-androgens, dacarbazin, hexamethylmelamine, hydroxyurea, mitotane, procarbazide, cisplastin, carboplatin, Melphalan, Methotrexate, and Chlorambucil.

Alternatively, the antibodies may carry a specific substance such as a metal ion (iron or zinc or other) into the tumor, and thus serve as a means or a carrier to deliver toxic substances (radioactive or cytotoxic chemical i.e. toxin like ricin or cytotoxic alkylating agent or cytotoxic prodrug, as mentioned before) to the tumor. The linkage of the antibody and the toxin or radioisotope can be chemical. Examples of direct linked toxins are doxorubicin, chlorambucil, ricin, pseudomonas exotoxin etc. A hybrid toxin can be generated with dual specificity, for the antigen and for the toxin. Such a bivalent molecule can serve to bind to the tumor and to deliver a cytotoxic drug to the tumor or to bind to and activate a cytotoxic lymphocyte such as binding to the $T_3$-$T_i$ receptor complex.

As shown in Examples 3, 4 and 6, and their respective figures, the antibodies of the invention are capable of inhibiting cell growth.

Thus, in a further aspect, the present invention provides a method of inhibiting cell growth, said method comprising contacting an effective amount of at least one anti-KTPAF50 antibody, or a combination thereof, or a composition comprising thereof, with cells. Said method may be an in vitro or ex vivo method.

As also shown in Example 6, the antibodies of the invention are capable of inhibiting cytokine expression, particularly TNF-α, IFN-γ or IL-10.

Thus, in another further aspect, the present invention provides a method for inhibiting cytokine expression, said method comprising contacting an effective amount of at least one anti-KTPAF50 antibody or a combination thereof, or a composition comprising thereof, with cells that express said cytokines. Said method may be an in vitro or ex vivo method.

In particular, the present invention provides a method for inhibiting pro-inflammatory cytokines.

Pro-inflammatory cytokines act by inducing inflammation. These cytokines either act as endogenous pyrogens (IL1, IL6, TNF-alpha), upregulate the synthesis of secondary mediators and pro-inflammatory cytokines by both macrophages and mesenchymal cells (including fibroblasts, epithelial and endothelial cells), stimulate the production of acute phase proteins, or attract inflammatory cells.

Pro-inflammatory cytokines include IL-1, TNF-α (Tumor Necrosis Factor α), INF-γ (Interferon γ), TNF-β, IL-4, IL-5, IL-6, IL-10 and IL-13. These cytokines are involved in the regulation of Th1 and Th2 lymphocytes.

Down regulation of TNF-α in particular has been shown to be important for the treatment of autoimmune diseases like rheumatoid arthritis, IBD and psoriasis.

Therefore, the anti-KTPAF50 antibodies of the invention, or compositions comprising thereof, are an extremely powerful tool for treating these human autoimmune diseases.

In this context, the antibodies of the invention may also be used in the treatment of graft rejection, as well as autoimmune diseases, neurode generative diseases and diabetes.

Thus, the present invention provides a method of treatment of conditions selected from the group consisting of cancer, autoimmune disorders, graft rejection, neurodegenerative disorders and diabetes, said method comprising administering a therapeutically effective amount of a KTPAF50-specific antibody, or a composition comprising thereof, to a subject in need.

Particular autoimmune diseases that may be treated with said antibodies are IBD, rheumatoid arthritis and psoriasis.

Neurodegenerative disorders are chronic and progressive disorders characterized by selective and symmetric loss of neurons in motor, sensory, or cognitive systems. A non-exhaustive list of neurodegenerative disorders includes Alzheimer's disease, Parkinson's disease, amyotrophic lateral sclerosis, Huntington's disease, Familial Amyloid Polyneuropathy, and Tauopathies.

Diabetes is characterized by high blood sugar, either because the organism does not produce enough insulin, or because the cells do not respond to the insulin that is produced. This high blood sugar produces the classical symptoms of polyuria (frequent urination), polydipsia (increased thirst) and polyphagia (increased hunger). The three main types of diabetes are: Type 1 diabetes, which results from the body's failure to produce insulin, and is treatable with the administration of insulin; Type 2 diabetes, which results from insulin resistance; and Gestational diabetes, in which pregnant women, who have never had diabetes before, have a high blood glucose level during pregnancy. Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

The present invention also provides a method that may be used in assessing prognosis of a cancer which has already been diagnosed. In particular, it is important to follow up pre-, during and post-treatment. Alternatively, said method is also appropriate for cancer screening, particularly when the sample to be tested is a blood sample, which is one of the most "patient-friendly" types of sample to be obtained from patients.

Thus, in another further aspect, the present invention provides a method for the diagnosis of cancer in a subject, said method comprising the steps of:
a. provided a sample from said subject;
b. contacting said sample with at least one antibody according to the invention, the anti-KTPAF50 antibody, or with a composition comprising thereof;
c. detecting the formation of a complex between said at least one antibody and its specific antigen, through detection means;
whereby the detection of a complex indicates that said subject suffers from cancer.

When referring herein to a subject, said subject may be a mammal, human or non-human. Non-human mammals include, but are not limited to, cows, horses, dogs, cats, mice, rats, guinea-pigs, etc. Usually the subject is a human, particularly a patient, or a healthy individual.

In one embodiment of the diagnostic method of the invention, said sample is a blood sample.

In a further embodiment of said diagnostic method of the invention, utilizing the anti-KTPAF50 antibody, or a composition comprising thereof, said cancer is selected from the group consisting of lung, breast and ovarian cancer.

Hence, the present invention also provides a method of monitoring the efficacy of cancer treatment. Monitoring the efficacy of treatment is essential for assessing prognosis of cancer treatment. Hence, the method of diagnostic presented herein may be effected in a subject before, during or after cancer treatment, and the analysis of the results obtained at each time point (the pattern of the relation between at least two antigen-antibody complexes) compared to the pattern of the same complexes in the normal population. The closest the pattern of the subject to that of the normal population, indicates a successful treatment.

Cancer treatment, as referred to herein, relates to any treatment for eradicating the disease, including radiotherapy, chemotherapy, etc.

The antibodies of the invention may also be used in multiplex immunoassays for high throughput screening of compounds that induce immune response in human and murine immune systems, as well as screening of compounds that induce inflammation and cancer in the digestive system especially, and other systems as well, wherein the antibodies of the invention may be used in combination with each other or in combination with other antibodies. Multiplex immunoassays are known to the man skilled in the art, and have been described, inter glia, by Anderson and Davison [Anderson and Davison (1999) Am. J. Pathol. 154:1017-1022].

As used herein to describe the present invention, "tumor", "cancer", "malignant proliferative disorder" and "malignancy" all relate equivalently to a hyperplasia of a tissue or organ. If the tissue is part of the lymphatic or immune systems, malignant cells may include non-solid tumors of circulating cells. Malignancies of other tissues or organs may produce solid tumors. In general, non-solid and solid tumors are, for example, carcinoma, melanoma, leukemia, and lymphoma.

Cancer and tumors include, but are not limited to, myeloid leukemia such as chronic myelogenous leukemia, acute myelogenous leukemia with maturation, acute promyelocytic leukemia, acute non-lymphocytic leukemia with increased basophiles, acute monocytic leukemia, acute myelomonocytic leukemia with eosinophilia, malignant lymphoma, such as Burkitt's non-Hodgkin's, lymphocytic leukemia, such as acute lymphoblastic leukemia, chronic lymphocytic leukemia, myeloproliferative diseases, solid tumors such as benign meningioma, mixed tumors of salivary gland, tumors in lip and oral cavity, pharynx, larynx, paranasal sinuses, colonic adenomas, adenocarcinomas, such as small cell lung cancer, kidney, uterus, prostate, bladder, ovary, colon, sarcomas, liposarcoma, myxoid, synovial sarcoma, rhabdomyosarcoma (alveolar), extraskeletal myxoid chondrosarcoma, Ewing's tumor, other include testicular and ovarian dysgerminoma, retinoblastoma, Wilms' tumor, neuroblastoma, malignant melanoma, mesothelioma, breast, skin, prostate, and ovarian cancer, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

The methods described herein for detection, diagnosis, assessment of prognosis, screening and treatment of cancer are suitable for any stage in cancer.

In another embodiment, the present methods are performed at any stage of cancer, and are most advantageous comparing to other currently used techniques especially for the diagnosis of cancer. When compared, e.g., to mammography, which technically causes great discomfort to the patient, besides having a relatively high degree of false positive results (which translates into numerous patients being submitted to further biopsy accompanied by unnecessary anxiety), the diagnostic method described in the present invention is based on a blood test, and has potentially a much smaller incidence of false positive results. All current macro-level diagnostic tools—mammogram, Digital Rectal Examination (DRE) and ultrasound (for breast, prostate and ovarian cancer, respectively) have the ability to diagnose cancer only after a suspicious tumor mass has already developed to a size that is visually detectable, resulting in lower survival rates and reduced quality of life for the patient. For example, for breast cancer, in the United States alone, around 30 million mammography procedures are undertaken annually and more than one million surgical breast biopsies are performed on women with suspicious breast lesions.

In that regard, it is important to be familiar with the systems of staging cancer. Staging is based on knowledge of the way cancer develops. Cancer cells divide and grow without control or order to form a tumor. As the tumor grows, it can invade nearby organs and tissues. Cancer cells can also break away from the tumor and enter the bloodstream or lymphatic system. By moving through the bloodstream or lymphatic system, cancer can spread from the primary site to form new tumors in other organs, which are denominated metastasis.

Most types of cancer have TNM (Tumor size, Nodes involvement, Metastasis) designations, but some do not. For example, cancers of the brain and spinal cord are classified according to their cell type and grade. Different staging systems are also used for many cancers of the blood or bone marrow, such as lymphoma. The Ann Arbor staging classification is commonly used to stage lymphomas and has been adopted by both the AJCC (American Joint Committee on Cancer) and the UICC (International Union Against Cancer). However, other cancers of the blood or bone marrow, including most types of leukemia, do not have a clear-cut staging system. Another staging system, developed by the International Federation of Gynecology and Obstetrics, is used to stage cancers of the cervix, uterus, ovary, vagina, and vulva. This system uses the TNM format. Additionally, childhood cancers are staged using either the TNM system or the staging criteria of the Children's Oncology Group, a group that conducts pediatric clinical trials.

The TNM staging system is as follows: T describes the size of the tumor and whether it has invaded nearby tissue, N describes any lymph nodes that are involved, and M describes the presence of metastasis.

Primary Tumor (T)
TX Primary tumor cannot be evaluated
T0 No evidence of primary tumor
Tis Carcinoma in situ (early cancer that has not spread to neighboring tissue)
T1,T2,T3,T4 Size and/or extent of the primary tumor
Regional Lymph Nodes (N)
NX Regional lymph nodes cannot be evaluated
N0 No regional lymph node involvement (no cancer found in the lymph nodes)

N1,N2, Involvement of regional lymph nodes (number and/or extent of N3 spread)
Distant Metastasis (M)
MX Distant metastasis cannot be evaluated
M0 No distant metastasis (cancer has not spread to other parts of the body)
M1. Distant metastasis (cancer has spread to other parts of the body)

An example according to the TNM system would be: breast cancer T3 N2 M0, referring to a large tumor that has spread outside the breast to nearby lymph nodes, but not to other parts of the body. Prostate cancer T2 N0 M0 means that the tumor is located only in the prostate and has not spread to the lymph nodes or any other part of the body.

Many cancer registries, such as the NCI's Surveillance, Epidemiology, and End Results Program (SEER), use summary staging. This system is used for all types of cancer. It groups cancer cases into five main categories:

In situ is early cancer that is present only in the layer of cells in which it began;
Localized is cancer that is limited to the organ in which it began, without evidence of spread;
Regional is cancer that has spread beyond the original (primary) site to nearby lymph nodes or organs and tissues;
Distant is cancer that has spread from the primary site to distant organs or distant lymph nodes;
Unknown is used to describe cases for which there is not enough information to indicate a stage.

Another commonly used staging system uses roman numerals:
Stage 0: Carcinoma in situ (early cancer that is present only in the layer of cells in which it began).
Stage I, II and III: Higher numbers indicate more extensive disease, greater tumor size and/or spread of the cancer to nearby lymph nodes and/or organs adjacent to the primary tumor.
Stage IV: The cancer has spread to another organ.

Thus, the method of diagnosis and detection of cancer provided by the present invention, e.g. using a labeled antibody as described herein, is also very useful for staging of the tumor [because the tumor changes as it grows]. E.g., it enables the detection and/or localization of growth where it is not detectable by other currently available techniques, especially at early stages of cancer.

Thus, in another further aspect, the present invention provides a method for the diagnosis of an auto-immune disease in a subject, said method comprising the steps of:
a. provided a sample from said subject;
b. contacting said sample with at least one antibody according to the invention, being an anti-KTPAF50 antibody, or with a composition comprising thereof;
c. detecting the formation of a complex between said at least one antibody and its specific antigen, through detection means;
whereby the detection of a complex indicates that said subject suffers from an auto-immune disease.

The above-described method may also be applied for the prognosis of an autoimmune disease, whereby detection of a complex, and comparing its levels during different timepoints during treatment (pre-treatment, during and post-treatment) provides an assessment of therapy efficiency and results in a subject suffering or potentially suffering from an auto-immune disease.

In one embodiment of said diagnostic method of the invention, said sample is a blood sample.

As defined herein "sample" refers to any sample obtained from a subject, generally a mammalian subject. Examples of biological samples include body fluids and tissue specimens. The source of the sample may be derived from such physiological media as blood, serum, plasma, breast milk, pus, cerebrospinal fluid, swabs, tissue scrapings, washings, urine, feces, rinse fluid obtained from wash of body cavities, phlegm, swabs taken from body regions (throat, vagina, ear, eye, skin, sores tissue, such as lymph nodes, or the like). Tissue specimens include biopsies of spleen, lymph nodes, and any lymphocyte-containing tissue.

The term "sample" in the present specification and claims is used herein in its broadest sense.

Typically swabs and samples that are a priori not liquid are contacted with a liquid medium which is then contacted with the detecting agent.

In one particular embodiment of the invention, said sample to be used in the method of the invention is any one of a body fluid or a culture-derived sample.

A culture-derived sample may be a cell extract, a medium sample, or a culture from a body fluid, e.g. a culture of a blood sample.

"Whole blood" means blood collected from an animal or human. Whole blood may be collected with heparin, EDTA, citrate or any other substance that prevents coagulation and clotting.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound antigen or label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Different carriers may be used for different antigens within the same tube. Alternatively, the surface may be flat such as a sheet, test strip, etc. Specific supports or carriers include polystyrene beads. Those skilled in the art will know many other suitable carriers for binding antibody or antigen, or will be able to ascertain the same by use of routine experimentation.

Other steps such as washing, stirring, shaking, filtering and the like may be added to the assays as is customary or necessary for the particular situation.

As defined herein, "culture medium" means any medium than can be used to sustain a sample to practice the present invention, including but not limited to RPMI 1640 with or without fetal calf (bovine) serum, preferably supplemented with appropriate antibiotics and glutamine, and optionally other additives, such as anti-fungal agents, non-essential amino acids, DTT, sodium pyruvate, etc. Other culture media which may be used in practicing the present invention include, but are not limited to, Eagles, Dulbecco's, McCoy's, Media 199, Waymouth's media, and serum free medium with or without supplement. In another embodiment the stimulant is without media.

The present invention also provides a method of treatment of cancer, comprising administering to a subject in need a therapeutically effective dosage of an antibody of the invention. In particular, said antibody when used for treatment is conjugated to a cytotoxic drug, or serves as a carrier for the delivery of toxic substances to the target cell. In this context, a target cell is a cell which is recognized by the antibody of the invention, which means a cell that expresses a tumor-associated antigen, and which therefore is associated with abnormal growth.

In another further aspect the present invention provides a kit for any one of diagnosis, monitoring treatment efficacy or assessing prognosis of cancer, said kit comprising the following components:

a. at least one antibody as described herein in the invention or a composition comprising thereof; and
b. instructions for carrying out the detection of the presence of an antigen in a sample, wherein said antigen is specifically recognized by said antibody.

Said kit may further comprise at least one of the following components:

a. at least one means for collecting a sample to be tested;
b. at least one reagent necessary for detection of said recognition of said antigen by said antibody; and
c. at least one control sample.

The present invention also provides a kit for the diagnosis and/or assessing prognosis of cancer.

The kit is essentially for the detection of tumor antigen specific antibodies in a subject. The subject may be a mammal, human or non-human. Usually the subject is a human patient, a cancer patient, or a healthy individual.

In a further aspect the present invention provides also a kit for at least one of diagnosis and monitoring treatment efficacy, and prognosis of an autoimmune disease, said kit comprising the following components:

a. at least one antibody as described herein in the invention, or a composition comprising thereof; and
b. instructions for carrying out the detection of the presence of an antigen in a sample, wherein said antigen is specifically recognized by said antibody.

Similarly, said kit may further comprise at least one of the following components:

a. at least one means for collecting a sample to be tested;
b. at least one reagent necessary for detection of said recognition of said antigen by said antibody; and
c. at least one control sample.

In one embodiment, any such kit is an antibody (or a recognizing agent) capture assay kit, as e.g. an ELISA kit, which comprises a solid support, at least one antibody as defined in the invention, and optionally secondary antibodies when appropriate. The kit may further optionally comprise any other necessary reagents such as detectable moieties, enzyme substrates and color reagents as described above. The antibody capture diagnostic kit is, alternatively, an immunoblot kit generally comprising the components and reagents described herein. The particular reagents and other components included in the diagnostic kits of the present invention can be selected from those available in the art in accord with the specific diagnostic method practiced in the kit. Such kits can be used to detect the antibody in biological samples, such as tissue or body fluid, particularly whole blood, PBMC or leucocytes before and/or after culture, obtained from a subject.

Where mentioned in the method of the invention suitable means, said suitable means may be an immune affinity procedure, an enzymatic assay, or means for detecting a structural feature, amongst others.

Where said suitable means are an immune affinity procedure, said procedure is any one of enzyme-linked immunosorbent assay (ELISA), Western Blot, immuno-precipitation, FACS, or any other immunoaffinity procedure utilizing the antibodies as described in the present invention.

In one particular embodiment, detection is effected through capture ELISA.

Capture ELISA (also known as "sandwich" ELISA) is a sensitive assay to quantify picogram to microgram quantities of substances (such as hormones, cell signaling chemicals, infectious disease antigens and cytokines). This type of ELISA is particularly sought after when the substance to be analyzed may be too dilute to bind to the polystyrene microtiter plate (such as a protein in a cell culture supernatant) or does not bind well to plastics (such as a small organic molecule). Optimal dilutions for the capture antibody, samples, controls, and detecting antibodies as well as incubation times are determined empirically and may require extensive titration. Ideally, one would use an enzyme-labeled detection antibody. However, if the detection antibody is unlabeled, the secondary antibody should not cross-react with either the coating antibody or the sample. The appropriate negative and positive controls should also be included.

The capture or coating antibody to be used should be diluted in carbonate-bicarbonate buffer or PBS. Capture antibodies are typically plated at 0.2 to 10 µg/ml. It is preferable to use affinity purified antibodies or at a minimum use an IgG fraction. Generally samples are diluted in PBS in the 10 ng-10 µg/well range (the more sensitive the assay, the less sample is required).

As used herein in the specification, the term "detectable moiety" refers to any atom, molecule or a portion thereof, the presence, absence or level of which may be monitored directly or indirectly. One example includes radioactive isotopes. Other examples include (i) enzymes which can catalyze color or light emitting (luminescence) reactions and (ii) fluorophores. The detection of the detectable moiety can be direct provided that the detectable moiety is itself detectable, such as, for example, in the case of fluorophores. Alternatively, the detection of the detectable moiety can be indirect. In the latter case, a second moiety which reacts with the detectable moiety, itself being directly detectable is preferably employed. The detectable moiety may be inherent to the antibody. For example, the constant region of an antibody can serve as an indirect detectable moiety to which a secondary antibody having a direct detectable moiety can specifically bind.

Thus, secondary antibodies are particular suitable means for the detection of the antibody in the method of the invention. This secondary antibody may be itself conjugated to a detectable moiety. One of the ways in which an antibody in accordance with the present invention can be detectably labeled is by linking the same to an enzyme. This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, horseradish peroxidase, alkaline phosphatase, malate dehydrogenase, staphylococcal nuclease, delta-5-steroid isomerase, yeast alcohol dehydrogenase, alpha-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase.

The detection can be accomplished by colorimetric methods, which employ a chromogenic substrate for the enzyme. Detection may also be accomplished by visual comparison of the extent of enzymatic reaction of a substrate in comparison with similarly prepared standards.

The solid support to which the first antibody is bound may be any water-insoluble, water-insuspensible, solid support. Examples of suitable solid support include large beads, e.g., of polystyrene, filter paper, test tubes, and microtiter plates. The first antibody may be bound to the solid support by covalent bonds or by adsorption. The advantage of the use of a solid support is that no centrifugation step is needed for the separation of solid and liquid phase.

The solid support mentioned above can include polymers, such as polystyrene, agarose, Sepharose, cellulose, glass beads and magnetizable particles of cellulose or other polymers. The solid-support can be in the form of large or small beads or particles, tubes, plates, or other forms.

As a solid support, use is preferably made of a test tube of a microtiter plate the inner walls of which are coated with a first antibody, e.g., the antibodies specific to, or of any fragment or derivative thereof prepared by the inventors for the present invention.

Reference to "determining" as used by the methods of the present invention, includes estimating, quantifying, calculating or otherwise deriving the amount of biomarker present in a specific sample. This may be achieved by measuring an end point indication that may be for example, the appearance of a detectable product, any detectable change in e.g. substrate levels or any change in the rate of the appearance of the product or the disappearance of the substrate, or measuring the amount of antibody bound to a biomarker as described by the invention.

In all of said test kits said means for collecting a sample to be tested can be a swab, a pipette, or similar collection means and said incubation means can be a liquid or semisolid culture medium placed in a plate, test tube, a glass or plastic surface, a well, or on a strip of absorbent paper, or similar means.

It should be appreciated that any version of the kit has been designed so as to also allow the test to be run on a scanner and the results fed into the computer in real time. This will ensure that the entire information can be mailed directly to all concerned and that it will be stored intact for any future reference.

In another embodiment of the kit, said sample is any one of a body fluid and a culture-derived sample.

The samples to be brought in contact with the antibodies of the invention may be arranged in an array.

The term "array" as used by the methods and kits of the invention refers to an "addressed" spatial arrangement of the recognition-agent, i.e., at least one of the antibodies of the invention. Each "address" of the array is a predetermined specific spatial region containing a recognition agent. For example, an array may be a plurality of vessels (test tubes), plates, micro-wells in a micro-plate each containing a different antibody. An array may also be any solid support holding in distinct regions (dots, lines, columns) different and known recognition agents, for example antibodies. The array preferably includes built-in appropriate controls, for example, regions without the sample, regions without the antibody, regions without either, namely with solvent and reagents alone and regions containing synthetic or isolated proteins or peptides recognized by the antibodies (positive control).

Solid support used for the array of the invention will be described in more detail herein after, in connection with the kits provided by the invention.

A solid support suitable for use in the kits of the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, filters, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, nylon, latex bead, magnetic bead, paramagnetic bead, superparamagnetic bead, starch and the like.

It should be further noted that any of the reagents included in any of the methods and kits of the invention may be provided as reagents embedded, linked, connected, attached placed or fused to any of the solid support materials described above.

It should be noted that any antibody used by the methods and kits of the invention may also be a polyclonal, monoclonal, recombinant, e.g., a chimeric, or single chain antibody (ScFv) derived from the antibodies of the invention.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

Unless defined otherwise, all technical and scientific terms used herein have the same meaning as commonly understood by one of ordinary skill in the art to which this invention is related.

EXAMPLES

Methods

A number of immunological techniques are not in each instance described herein in detail, like for example ELISA, as they are well known to the person of skill in the art, and these are described in detail in e.g., Harlow and Lane (1988) Antibodies: a laboratory manual, Cold Spring Harbour Laboratory.

General Methods of Molecular Biology

A number of methods of the molecular biology art are not detailed herein, as they are well known to the person of skill in the art. Such methods include PCR, expression of cDNAs, transfection of human cells, and the like. Textbooks describing such methods are, e.g., Sambrook et al. (1989) *Molecular Cloning, A Laboratory Manual*, Cold Spring Harbor Laboratory, ISBN: 0879693096; F. M. Ausubel (1988) *Current Protocols in Molecular Biology*, ISBN: 047150338X, John Wiley & Sons, Inc. Furthermore, a number of immunological techniques are not in each instance described herein in detail, like for example Western Blot, as they are well known to the person of skill in the art. See, e.g., Harlow and Lane (1988) *Antibodies: a laboratory manual*, Cold Spring Harbor Laboratory.

ELISA General Protocol

Enzyme-linked Immunosorbent Assays (ELISAs) combine the specificity of antibodies with the sensitivity of simple enzyme assays, by using antibodies or antigens coupled to an easily-assayed enzyme. ELISAs can provide a useful measurement of antigen or antibody concentration. An ELISA is a five-step procedure: 1) microtiter plate wells are coated with antigen diluted in PBS, incubated overnight at 4C and washed; 2) unbound sites are blocked in BSA/FCS in PBS to prevent false positive results, incubated for 1 h and washed; 3) antibody is added to the wells, incubated for 1 h and washed; 4) anti-human IgG conjugated to an enzyme is added, incubated for 1 h and washed; 5) the reaction of the substrate with the enzyme produces a coloured product, finally, indicating a positive reaction.

FACS Protocol

1. Cells were harvested, washed and adjusted in suspension to a concentration of $1-5 \times 10^6$ cells/ml in ice cold PBS, 10% FCS, 1% sodium azide.
2. 0.1-10 µg/ml of the primary labelled antibody was added. If necessary, the antibody was diluted in 3% BSA/PBS
3. Cells+antibody were incubated for at least 30 min at room temperature or 4° C.
4. The cells were washed 3 times by centrifugation at 400 g for 5 minutes and resuspended in 500 µl to 1 ml of ice cold PBS, 10% FCS, 1% sodium azide.
5. The cells were then ready to be analyzed with the flow cytometer.

ELISA Procedure for the Detection of KTPAF50:
1. Calibration curve: Serial dilutions of PRT3 were prepared in PBS (Biological Industries, Catalog No. 02-023-5A) from 2000 pg/ml to 31 pg/ml.
2. Samples were quickly thawed in a 37° C. bath.
3. 70 µl duplicates of each blood sample (not diluted) and 70 µl triplicates of the standard samples were loaded in a Maxisorp 96-well plate (NUNC, F96 Maxisorp, Catalog No. 442404), and incubated at 4° C. overnight with shaking.
4. Washing: Plates were washed 4 times with 300 µl 0.05% TW-20 (Amresco, Catalog No. 0777-1L) in PBS.
5. Blocking: 300 µl of blocking buffer 5% BSA (MP biomedicals, Catalog No. 160069) in PBS was loadedto each well, and incubated at room temperature for 1 hour with shaking.
6. Washing: Same as step #4.
7. Detection: KTPAF50-specific antibody was diluted (affinity purified) 1:250 in diluent (0.05% TW-20, 0.1% BSA in PBS). 100 µl of detection antibody were loaded in each well and incubated at room temperature for 2 hours with shaking.
8. Washing: Same as step #4 above.
9. HRP conjugate: Goat anti-rabbit HRP conjugate antibody (Cell signaling, Catalog No. 7074) was diluted 1:200 in diluent. 100 µl of HRP conjugate was loaded in each well and incubated for 30 minutes at room temperature with shaking.
10. Washing: Same as step #4 above, with 5 washings instead of 4.
11. Development: 100 µl TMB (3,3',5,5'-tetramethybenzidine, Horseradish peroxidase substrate, Millipore, Catalog No. ES001-500mL) was added to each well. With development of blue color, 50 µl $2NH_2SO_4$ (Frutarom, Catalog No. 5552540) were added.
12. Plate reading: In a microplate reader, absorbance was checked at 450 nm.

Preparation of Polyclonal Antibodies

Polyclonal antibodies were produced in rabbits using the standard protocol for the preparation of polyclonal antibodies.

The antigen used in the preparation of the KTPAF50-specific polyclonal antibody was a peptide corresponding to the last 14 amino acids at the C-terminus of the KTPAF50 protein (EKGAAFSPIYPRRK), corresponding to the sequence denoted by SEQ ID NO. 3.

FIG. 1 shows the curve of specificity of the KTPAF50-specifc antibody for its antigen.

Preparation of KTPAF50-Specific Monoclonal Antibodies and Calibration

Monoclonal antibodies against KTPAF50 were custom-made by Genemed Synthesis, Inc. (San Antonio, Tex., USA) according to standard protocol known to the man skilled in the art of antibodies. Calibration of antibody affinity was performed by ELISA, as follows:

1. KTPAF50 peptide was diluted in PBS to 1000, 500, 100 and 0 ng/ml to create a calibration curve. These concentrations were loaded 30 times in duplicates on two MAX-ISORP™ ELISA Nunc Immuno™ plates (Nunc #442404). The plates were incubated overnight at 4° C. with gentle shaking.
2. After incubation, the plates were washed 4 times using 0.05% Tween-20 in PBS (300 µl/well).
3. Wells were blocked by loading 300 µl/well 1% BSA in PBS, followed by overnight incubation at 4° C. with gentle shaking.
4. After incubation, the plates were washed as described in step 2. 100 µl of each of the 30 monoclonal KTPAF50 antibodies were loaded in duplicates in each KTPAF50 dilution curves. As a control, a polyclonal KTPAF50 antibody (diluted 1:250) was also loaded on each plate, and the plates were incubated for 1 hour at 37° C.
5. After incubation, the plates were washed as described in step 2. 50 µl of 1:200 Peroxidase-AffiniPure Goat Anti-Mouse IgG (Jackson ImmunoResearch #115-035-206) diluted in 0.1% BSA, 0.05% Tween-20 in PBS was loaded in each well. Plates were incubated for 1 hour at 37° C.
6. After incubation, the plates were washed as described in step 2. 100 µl TMB/E (Millipore #ES001-500mL) were loaded in each well and incubated for 15 minutes at 37° C.
7. 50 µl N $H_2SO_4$ was loaded in each well.
8. Plates were read using a microplate reader at 450 nm.

TDS Protocol (from eBioscience™)
1. Corning Costar 9018 ELISA plates were coated with 100 µl/well of capture antibody in Coating Buffer (dilute as noted on Certificate of Analysis, which is included with the reagent set). The plates were sealed and incubated overnight at 4° C.
2. Wells were aspirated and washed 5 times with >250 µl/well Wash Buffer. Allowing time for soaking (~1 minute) during each wash step increased the effectiveness of the washes. Residual buffer was removed from the plate on absorbent paper.

3. 1 part 5× concentrated Assay Diluent was diluted with 4 parts DI water. Wells were blocked with 200 µl/well of 1× Assay Diluent, and incubated at room temperature for 1 hour.
4. The washes were repeated 5 times.
5. For the standard curve, 100 µl/well of diluted standard was added to the appropriate wells and 2-fold serial dilutions were prepared from the top standards to make the standard curve. 100 µl/well of the samples were added to the appropriate wells. Plates were covered or sealed and incubated at room temperature for 2 hours (or overnight at 4° C. for maximal sensitivity).
6. The washes were repeated 5 times.
7. 100 µl/well of detection antibody diluted in 1× Assay Diluent* was added. The plate was sealed and incubated at room temperature for 1 hour.
8. The washes were repeated 5 times.
9. 100 µl/well of Avidin-HRP* diluted in 1× Assay Diluent was added. The plates were sealed and incubated at room temperature for 30 minutes.
10. In the last wash, the wells were soaked in Wash Buffer for 1 to 2 minutes prior to aspiration, and the wash repeated for a total of 7 times.
11. 50 µl of Stop Solution 100 µl/well of Substrate Solution was added to each well. Plates were incubated at room temperature for 15 minutes, and the reaction stopped with 50 µl of stop solution.
12. Plates were read at 450 nm. If wavelength subtraction was available, the values of 570 nm were substracted from those of 450 nm and the data analyzed.

Procedure for Thawing Poietics® Cells

DNase I functions to prevent clumping of culture cells, and mononuclear cells, and was added to medium.
1. Vials of frozen cells were quickly thawed in a 37° C. water bath.
2. A maximum of 2 ml of cell suspension were aseptically transferred to a 50 ml conical tube.
3. Vials were rinsed with 1 ml of pre-warmed medium containing 10% FBS or 1% BSA, and DNase I at 20 U/ml.
4. Total volume was 5 ml, while gently swirling after each addition of several drops of medium (=three minutes).
5. Volume up completed by adding 1 ml to 2 ml volumes of medium dropwise, while gently swirling after each addition of medium (=five to ten minutes).
6. The cell suspension was centrifuged at 200×g at room temperature for 15 minutes.
7. The cell pellet was gently resuspended in the remaining medium.
8. The volume was slowly brought up with wash medium to fill the tube by adding 1 ml to 2 ml volumes of medium while gently swirling after each addition of medium.
9. Cell suspensions were centrifuged at 200×g at room temperature for 15 minutes.
10. 2 ml of the wash Was carefully removed and the cell pellet gently resuspended in the remaining 2 ml of medium. Cells were counted. If cell count was lower than expected, a further wash can be done in the supernatant saved from step 7 and the cells combined if necessary.
11. The cells rested for one hour at 37° C. and 5% CO2, counted a second time, and then put in culture.

*For the addition of DNase, 20 ml of medium containing 10% FBS and 20 U/ml of DNase I (Sigma D 4513) should be prepared. DNase-containing medium was used to dilute the cells.

Animals

Balb/C mice were Purchased from Harlan Israel.

Sequences Referred to in the Present Application

| SEQ. ID. No. | Sequence | Description |
|---|---|---|
| SEQ. ID. No. 1 | LRRREQAERGSRRCAIAG EERAMLSPSPLPETPFSP EKGAAFSPIYPRRK | KTPAF50 full-length (without signal peptide) |
| SEQ. ID. No. 2 | MPGHSRLLSILVSGLCVV GSSIGVLRRREQAERGSR RCAIAGEERAMLSPSPLP ETPFSPEKGAAFSPIYPR RK | KTPAF50 full-length |
| SEQ. ID. No. 3 | EKGAAFSPIYPRRK | C-terminal peptide |
| SEQ. ID. No. 4 | LRRREQAERGSRRCAIAG EERAMLSPSPLPETPFSP | N-terminal peptide |
| SEQ. ID. No. 5 | LRRREQAERGSRRC | N-terminal peptide |
| SEQ. ID. No. 6 | PEKGAAFSPIYPRRKC | C-terminal peptide |
| SEQ. ID. No. 7 | CAIAGEERAMLSPSP | peptide aa 38-52 |

Example 1

Detection of KTPAF50 in Human Blood Samples

Nineteen human blood serum samples were obtained from Asterand®, from men and women aged 50-65 years old: 9 samples of patients with lung cancer, and 10 healthy individuals. All the samples were kept under −80° C. until use.

The blood samples were tested for the presence of KTPAF50 protein using the polyclonal anti-KTPAF50 antibody. As may be seen in FIG. 2, expression of KTPAF50 was significantly higher in lung cancer samples.

Thus, anti-KTPAF50 antibody may be used as a diagnostic tool for the detection of lung cancer.

Example 2

Generation of Anti-KTPAF50-Specific Monoclonal Antibodies

KTPAF50-specific monoclonal antibodies were generated using a KTPAF50 peptide (Antigens 1, 2 or 3, see table below) or full length KTPAF50 protein as antigen. The antigens are specified in Table 1 below. Antigen2 is essentially the same used for the preparation of the polyclonal antibodies, with a proline at its N-terminus and a cysteine at its C-terminus. The antibodies were commissioned from Genemed Synthesis, Inc. (San Antonio, Tex., USA).

TABLE 1

Antigens used to generate the monoclonal antibodies

| Antigen | Name | SEQ. ID. NO. | Sequence |
|---|---|---|---|
| Antigen1 | Peptide #1 | SEQ. ID. NO. 5 | LRRREQAERGSRRC |
| Antigen2 | Peptide #2 | SEQ. ID. NO. 6 | PEKGAAFSPIYPRRKC |
| Antigen3 | Peptide #3 | SEQ. ID. NO. 7 | CAIAGEERAMLSPSP |

TABLE 1-continued

Antigens used to generate the monoclonal antibodies

| Antigen | Name | SEQ. ID. NO. | Sequence |
|---|---|---|---|
| Antigen4 | Protein 81869 | SEQ. ID. NO. 1 | LRRREQAERGSR-RCAIA GEERAMLSPSPL-PETPF SPEKGAAFSPIYPRRK |

30 different monoclonal antibodies were produced by Genemed Synthesis, Inc. (San Antonio, Tex., USA) and their affinity to KTPAF50 verified.

Table 2 summarizes the antigen specificity of each hybridoma.

TABLE 2

Antigen specificity of hybridomas

| Hybridoma | Antigen |
|---|---|
| 2B6A3 | Antigen2 (SEQ. ID NO. 6) |
| 2B6A12 | Antigen2 (SEQ. ID NO. 6) |
| 2B6G2 | Antigen2 (SEQ. ID NO. 6) |
| 2B6H1 | Antigen2 (SEQ. ID NO. 6) |
| 5E11B5 | Antigen2 (SEQ. ID NO. 6) |
| 5E11B8 | Antigen2 (SEQ. ID NO. 6) |

TABLE 2-continued

Antigen specificity of hybridomas

| Hybridoma | Antigen |
|---|---|
| 5E11H3 | Antigen2 (SEQ. ID NO. 6) |
| 5E11H5 | Antigen2 (SEQ. ID NO. 6) |
| 3E1F9 | Antigen2 (SEQ. ID NO. 6) |
| 3E1F11 | Antigen2 (SEQ. ID NO. 6) |
| 3E1G4 | Antigen2 (SEQ. ID NO. 6) |
| 3E1G6 | Antigen2 (SEQ. ID NO. 6) |
| 2A8B8 | Antigen2 (SEQ. ID NO. 6) |
| 2A8B12 | Antigen2 (SEQ. ID NO. 6) |
| 2A8H7 | Antigen2 (SEQ. ID NO. 6) |
| 6E2B6 | Antigen3 (SEQ. ID NO. 7) |
| 6E2C5 | Antigen3 (SEQ. ID NO. 7) |
| 6E2C9 | Antigen3 (SEQ. ID NO. 7) |
| 6E2D4 | Antigen3 (SEQ. ID NO. 7) |
| 7D4D6 | Antigen3 (SEQ. ID NO. 7) |
| 7D4E12 | Antigen3 (SEQ. ID NO. 7) |
| 7D4F9 | Antigen3 (SEQ. ID NO. 7) |
| 7D4H10 | Antigen3 (SEQ. ID NO. 7) |
| 6F5A1 | Antigen3 (SEQ. ID NO. 7) |
| 6F5B6 | Antigen3 (SEQ. ID NO. 7) |
| 6F5C9 | Antigen3 (SEQ. ID NO. 7) |
| 6F5C12 | Antigen3 (SEQ. ID NO. 7) |
| 3E3B3 | Antigen3 (SEQ. ID NO. 7) |
| 3E3C8 | Antigen3 (SEQ. ID NO. 7) |
| 3E3G7 | Antigen3 (SEQ. ID NO. 7) |

The results of the affinity calibration curves to each monoclonal antibody are summarized in Table 3.

TABLE 3

Calibration of anti-KTPAF50 monoclonal antibodies

| MAB 1 (6E2B6) | | | | | MAB 2 (6E2C5) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.616 | 0.555 | 0.065 | 72 | 1000 | 0.455 | 0.61 | 0.159 | 183 |
| 500 | 0.613 | 0.329 | −0.050 | 335 | 500 | 0.205 | 0.209 | −0.167 | 5 |
| 100 | 0.518 | 0.319 | −0.102 | 235 | 100 | 0.173 | 0.173 | −0.201 | 0 |
| 0 | 0.662 | 0.379 | 0.521 | 334 | 0 | 0.378 | 0.369 | 0.374 | 11 |

| MAB 3 (6E2C9) | | | | | MAB 4 (6E2D4) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.903 | 1.073 | 0.468 | 200 | 1000 | 1.1 | 1.135 | 0.744 | 41 |
| 500 | 0.219 | 0.209 | −0.307 | 12 | 500 | 0.233 | 0.199 | −0.158 | 40 |
| 100 | 0.173 | 0.21 | −0.329 | 44 | 100 | 0.299 | 0.177 | −0.136 | 144 |
| 0 | 0.426 | 0.355 | 0.391 | 84 | 0 | 0.274 | 0.261 | 0.268 | 15 |

| MAB 5 (7D4D6) | | | | | MAB 6 (7D4E12) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 1.076 | 1.222 | 0.925 | 172 | 1000 | 1.101 | 1.026 | 0.731 | 88 |
| 500 | 0.223 | 0.295 | 0.035 | 85 | 500 | 0.38 | 0.461 | 0.088 | 95 |
| 100 | 0.178 | 0.175 | −0.048 | 4 | 100 | 0.224 | 0.328 | −0.057 | 123 |
| 0 | 0.204 | 0.245 | 0.225 | 48 | 0 | 0.23 | 0.436 | 0.333 | 243 |

| MAB 7 (7D4F9) | | | | | MAB 8 (7D4H10) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.812 | 0.474 | 0.419 | 398 | 1000 | 0.437 | 0.498 | 0.135 | 72 |
| 500 | 0.405 | 0.147 | 0.052 | 304 | 500 | 0.148 | 0.128 | −0.195 | 24 |
| 100 | 0.211 | 0.147 | −0.046 | 75 | 100 | 0.098 | 0.102 | −0.233 | 5 |
| 0 | 0.398 | 0.189 | 0.294 | 246 | 0 | 0.161 | 0.115 | 0.138 | 54 |

TABLE 3-continued

Calibration of anti- KTPAF50 monoclonal antibodies

| MAB 9 (6F5A1) | | | | | MAB 10 (6F5B6) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.655 | 0.751 | 0.521 | 113 | 1000 | 0.693 | 0.493 | 0.433 | 236 |
| 500 | 0.142 | 0.13 | −0.046 | 14 | 500 | 0.158 | 0.178 | 0.007 | 24 |
| 100 | 0.135 | 0.126 | −0.052 | 11 | 100 | 0.135 | 0.145 | −0.021 | 12 |
| 0 | 0.2 | 0.164 | 0.182 | 42 | 0 | 0.183 | 0.138 | 0.161 | 53 |

| MAB 11 (6F5C9) | | | | | MAB 12 (6F5C12) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.476 | 0.659 | 0.386 | 216 | 1000 | 3.147 | 3.168 | 2.997 | 25 |
| 500 | 0.197 | 0.224 | 0.029 | 32 | 500 | 2.468 | 2.501 | 2.324 | 39 |
| 100 | 0.155 | 0.184 | −0.013 | 34 | 100 | 2.874 | 2.656 | 2.605 | 257 |
| 0 | 0.155 | 0.162 | 0.159 | 8 | 0 | 0.197 | 0.743 | 0.470 | 643 |

| MAB 13 (3E3B3) | | | | | MAB 14 (3E3C8) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | ??? | ??? | #DIV/0! | #DIV/0! | 1000 | ??? | ??? | #DIV/0! | #DIV/0! |
| 500 | ??? | ??? | #DIV/0! | #DIV/0! | 500 | ??? | ??? | #DIV/0! | #DIV/0! |
| 100 | ??? | ??? | #DIV/0! | #DIV/0! | 100 | 4.063 | 4.104 | 3.710 | 0.029 |
| 0 | 0.711 | 0.209 | 0.460 | 0.355 | 0 | 0.145 | 0.126 | 0.136 | 0.013 |

| MAB 15 (3E3G7) | | | | | MAB 16 (2B6A3) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | ??? | ??? | #DIV/0! | #DIV/0! | 1000 | 0.436 | 0.304 | −0.004 | 0.093 |
| 500 | ??? | ??? | #DIV/0! | #DIV/0! | 500 | 0.105 | 0.1 | −0.271 | 0.004 |
| 100 | 3.959 | 3.918 | 3.418 | 0.029 | 100 | 0.098 | 0.104 | −0.273 | 0.004 |
| 0 | 0.131 | 0.125 | 0.128 | 0.004 | 0 | 0.118 | 0.116 | 0.117 | 0.001 |

| MAB 17 (2B6A12) | | | | | MAB 18 (2B6G2) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.301 | 0.285 | 0.069 | 0.011 | 1000 | 0.389 | 0.57 | 0.147 | 0.128 |
| 500 | 0.12 | 0.125 | −0.102 | 0.004 | 500 | 0.152 | 0.35 | −0.082 | 0.140 |
| 100 | 0.108 | 0.106 | −0.118 | 0.001 | 100 | 0.143 | 0.363 | −0.080 | 0.156 |
| 0 | 0.133 | 0.124 | 0.129 | 0.006 | 0 | 0.203 | 0.487 | 0.345 | 0.201 |

| MAB 19 (2B6H1) | | | | | MAB 20 (5E11B5) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.41 | 0.295 | 0.128 | 0.081 | 1000 | 0.381 | 0.331 | 0.023 | 0.035 |
| 500 | 0.233 | 0.316 | 0.050 | 0.059 | 500 | 0.297 | 0.313 | −0.028 | 0.011 |
| 100 | 0.223 | 0.244 | 0.009 | 0.015 | 100 | 0.312 | 0.238 | −0.058 | 0.052 |
| 0 | 0.244 | 0.374 | 0.309 | 0.092 | 0 | 0.259 | 0.221 | 0.240 | 0.027 |

| MAB 21 (5E11B8) | | | | | MAB 22 (5E11H3) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.435 | 0.404 | 0.238 | 0.022 | 1000 | 0.483 | 0.463 | 0.313 | 0.014 |
| 500 | 0.53 | 0.405 | 0.286 | 0.088 | 500 | 0.444 | 0.451 | 0.287 | 0.005 |
| 100 | 0.291 | 0.256 | 0.092 | 0.025 | 100 | 0.311 | 0.274 | 0.132 | 0.026 |
| 0 | 0.3 | 0.203 | 0.252 | 0.069 | 0 | 0.218 | 0.282 | 0.250 | 0.045 |

| MAB 23 (5E11H5) | | | | | MAB 24 (3E1F9) | | | | |
|---|---|---|---|---|---|---|---|---|---|
| KTPAF50 (ng/ml) | 1 | 2 | mean-zero | STD dev | KTPAF50 (ng/ml) | 1 | 2 | mean-zero | STD dev |
| 1000 | 0.369 | 0.437 | 0.221 | 0.048 | 1000 | 0.354 | 0.377 | 0.205 | 0.016 |
| 500 | 0.357 | 0.376 | 0.185 | 0.013 | 500 | 0.484 | 0.369 | 0.266 | 0.081 |

TABLE 3-continued

Calibration of anti- KTPAF50 monoclonal antibodies

| 100 | 0.276 | 0.288 | 0.100 | 0.008 | 100 | 0.462 | 0.336 | 0.239 | 0.089 |
|---|---|---|---|---|---|---|---|---|---|
| 0 | 0.222 | 0.297 | 0.260 | 0.053 | 0 | 0.433 | 0.364 | 0.399 | 0.049 |

| MAB 25 (3E1F11) | | MAB 26 (3E1G4) | | MAB 27 (3E1G6) | | MAB 28 (2A8B8) | |
|---|---|---|---|---|---|---|---|
| KTPAF50 (ng/ml) | 1 | KTPAF50 (ng/ml) | 1 | KTPAF50 (ng/ml) | 1 | KTPAF50 (ng/ml) | 1 |
| 1000 | 0.37 | 1000 | 0.293 | 1000 | 0.254 | 1000 | 0.156 |
| 500 | 0.293 | 500 | 0.273 | 500 | 0.232 | 500 | 0.422 |
| 100 | 0.355 | 100 | 0.246 | 100 | 0.183 | 100 | 0.208 |
| 0 | 0.655 | 0 | 0.676 | 0 | 0.652 | 0 | 0.651 |

| MAB 29 (2A8B12) | | MAB 30 (2A8H7) | |
|---|---|---|---|
| KTPAF50 (ng/ml) | 1 | KTPAF50 (ng/ml) | 1 |
| 1000 | 0.666 | 1000 | 0.285 |
| 500 | 0.379 | 500 | 0.694 |
| 100 | 0.326 | 100 | 0.232 |
| 0 | 0.696 | 0 | 0.88 |

* ??? means the value is above the reader's range

Example 3

Effect of Monoclonal KTPAF50 Antibodies on Viability of Female Balb/C Splenocytes 30 KTPAF50-specific monoclonal antibodies were tested for their effect on splenocyte viability. Viability was tested using the resazurin assay.

Procedure:
1. One female Balb/C (20 weeks old) spleen was harvested and the red blood cells were lysed using 1×RBC Lysis Buffer (eBioscience #00-4333).
2. The cells were divided to two F96 MicroWell™ Plates (Nunc #167008). In each plate 5×5 wells were loaded with 50,000 cells in 200 µl Karyotyping medium (Biological industries 01-201-1B). Cells were incubated for 24 hours in 37° C., 5% $CO_2$.
3. After incubation the following treatments were added to each well in quintuplicate:
   a. Control (anti-p53 antibody [Santa Cruz CS-65334]- 10 µl)
   b. 100 ng/ml KTPAF50
   c. 1000 ng/ml KTPAF50
   d. 15 µl of α-KTPAF50 1 (hybridoma 3E3G7)
   e. 15 µl of α-KTPAF50 2 (hybridoma 5E11H3)
4. The first plate was incubated for 24 hours and the second for 48 hours in 37° C., 5% $CO_2$.

After the incubation time, 20 µl of Resazurin (R&D systems #AR002) was added to each well, and the wells fluorescence (530/590 nm) were checked using a plate reader at 4 and 24 hours.

Figure 3A:
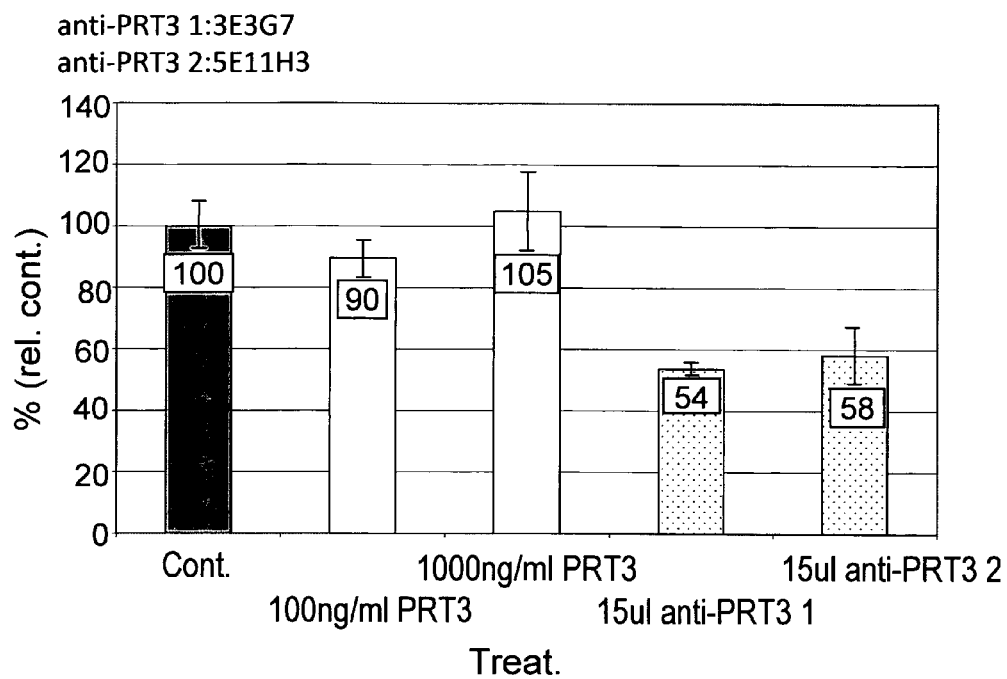
FIG. 3A-3C: Effect of anti-KTPAF50 monoclonal antibodies on female Balb/C splenocyte viability
Figure 3B:
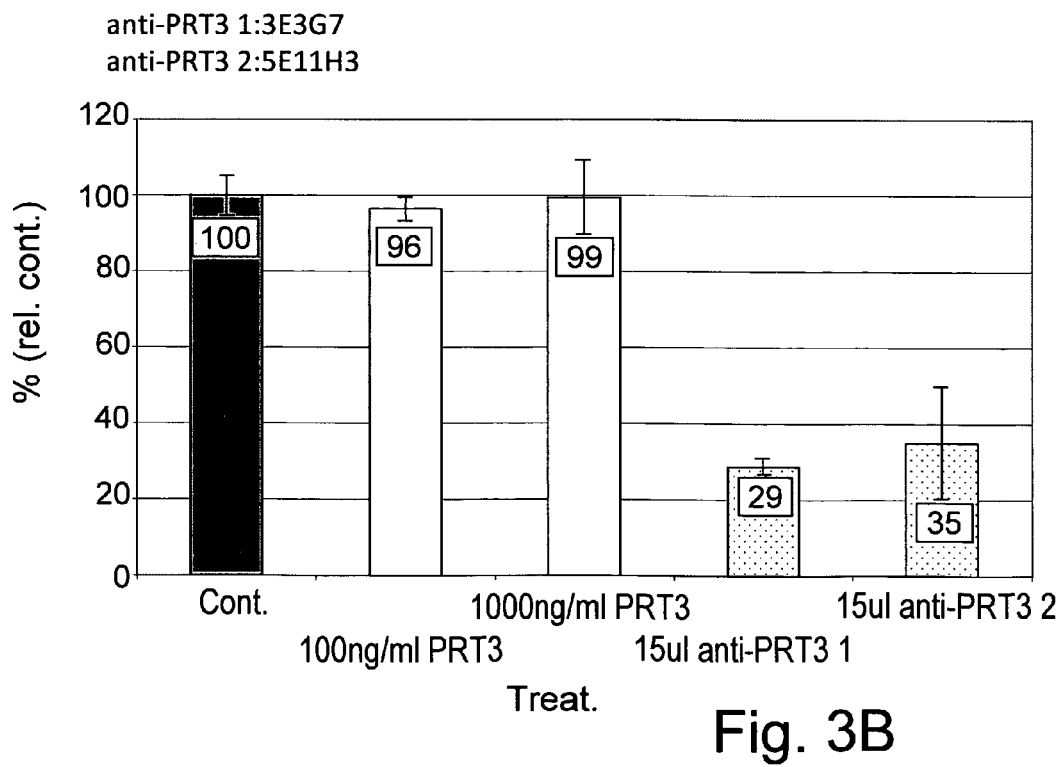
Figure 3C:
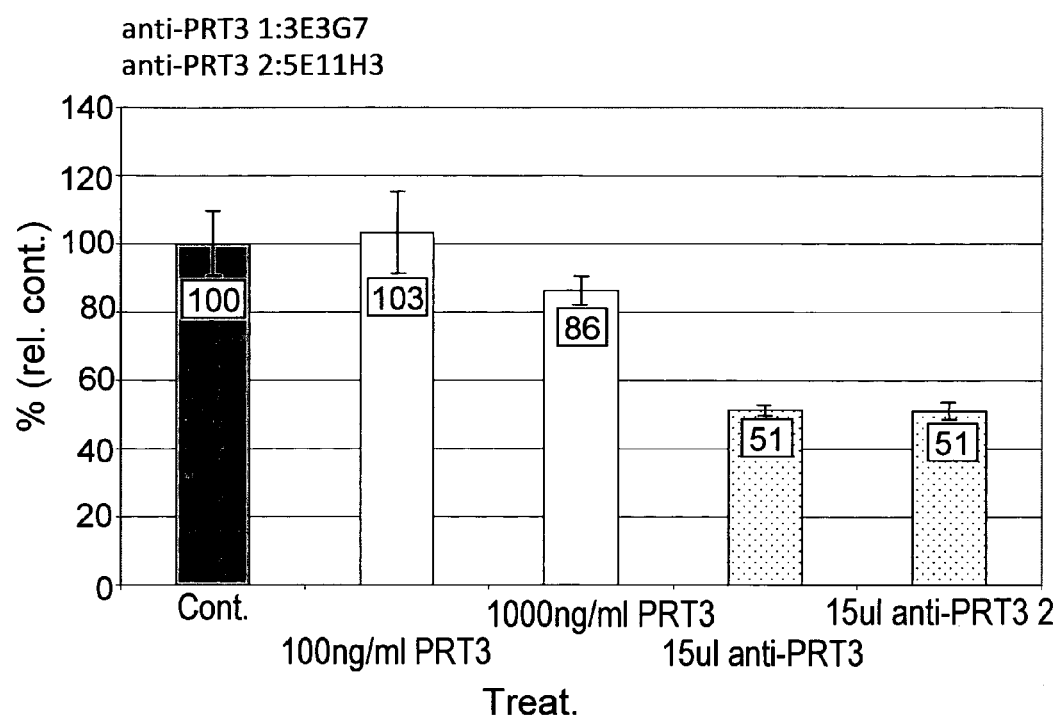

The results are shown in FIGS. 3A-3C. Essentially, after 24 hours of treatment and 4-hour incubation with Resazurin, cell viability was reduced to 54% and 58%, in cultures treated with 3E3G7 and 5E11H3, respectively (FIG. 6A). The reduction in cell viability was even more prominent following 24-hour incubation with Resazurin, 29% and 35%, respectively in cultures treated with 3E3G7 and 5E11H3, respectively (FIG. 6B).

A 48-hour treatment with the KTPAF50-specific antibodies reduced cell viability to an extent similar to the 24-hour treatment (FIG. 6C).

The results clearly show that monoclonal antibodies against KTPAF50 can dramatically reduce the viability of Balb/C splenocytes, suggesting that KTPAF50 plays a pivotal role in keeping the viability of mice splenocytes. Neutralizing KTPAF50 activity with specific monoclonal antibodies can serve as a very strong tool for treating autoimmune diseases induced in mice. Similarly, KTPAF50-specific monoclonal antibodies shall be used in human clinical trials.

Example 4

Effect of Monoclonal KTPAF50 Antibodies on Viability of C57/Black Splenocytes

30 KTPAF50-specific monoclonal antibodies were tested for their effect on splenocyte viability. Viability was tested using the resazurin assay.

Procedure:
1. One female and one male C57/black (8 weeks old) spleen was harvested and the red blood cells were lysed using 1×RBC Lysis Buffer (eBioscience #00-4333).
2. The cells were divided to two F96 MicroWell™ Plates (Nunc #167008). In each plate 5×5 wells were loaded with 50,000 cells in 200 µl Karyotyping medium (Biological industries 01-201-1B). Cells were incubated for 24 hours in 37° C., 5% $CO_2$.
3. After incubation the following treatments were added to each well in quintuplicate:
   a. Control (anti-p53 antibody [Santa Cruz CS-65334]- 10 µl)
   b. 15 µl of anti-KTPAF50 1 (antibody 5E11H3)
   c. 15 µl of anti-KTPAF50 2 (antibody 3E3G7)
   d. 100 ng/ml KTPAF50
   e. 500 ng/ml KTPAF50
4. The first plate was incubated for 24 hours, the second for 48 hours and the third for 72 hours, in 37° C. at 5% $CO_2$.
5. After the incubation time, 20 µl of Resazurin (R&D systems #AR002) was added to each well, and fluorescence (530/590 nm) measured using a plate reader at 4 and 24 hours.

Figure 4A:
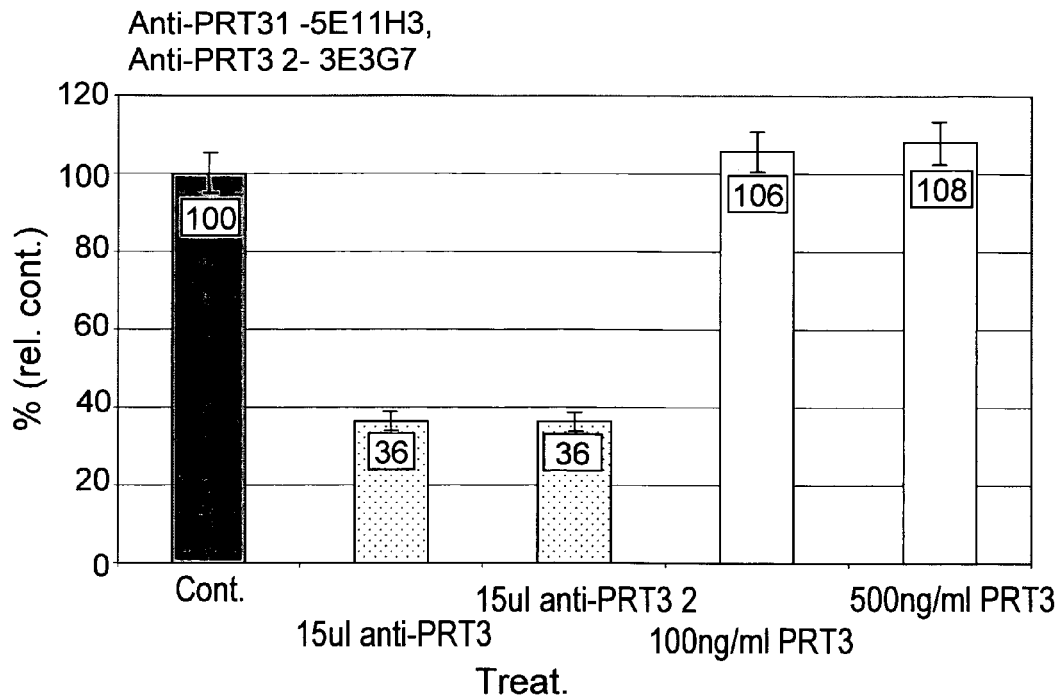
FIG. 4A-4F: Effect of anti-KTPAF50 monoclonal antibodies on female or male C57/black splenocyte viability
Figure 4B:
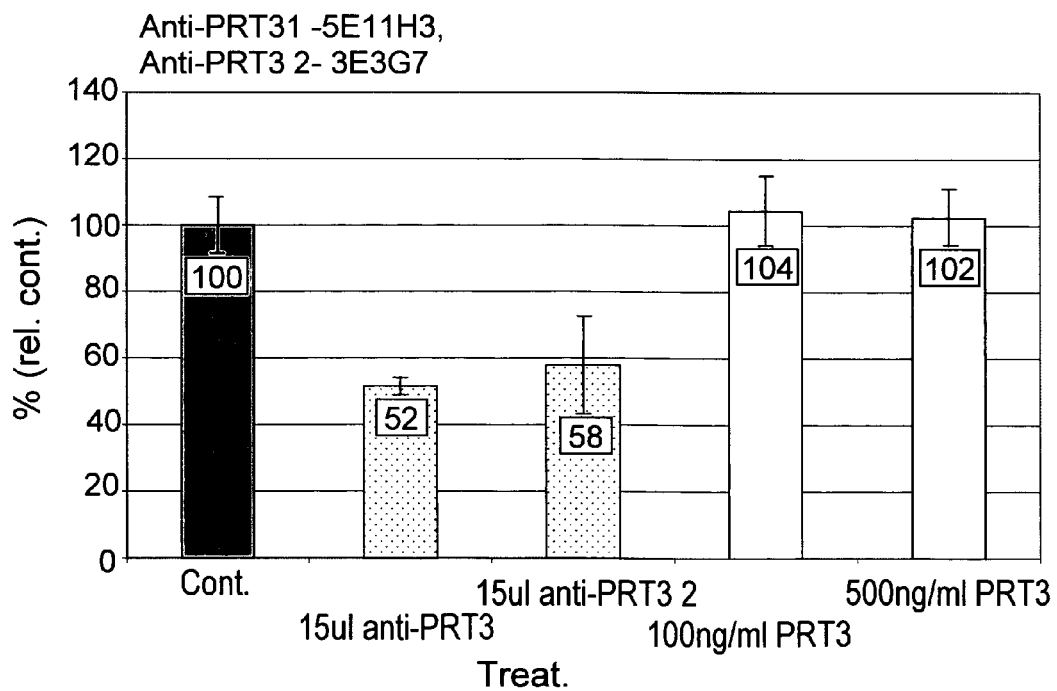
Figure 4C:
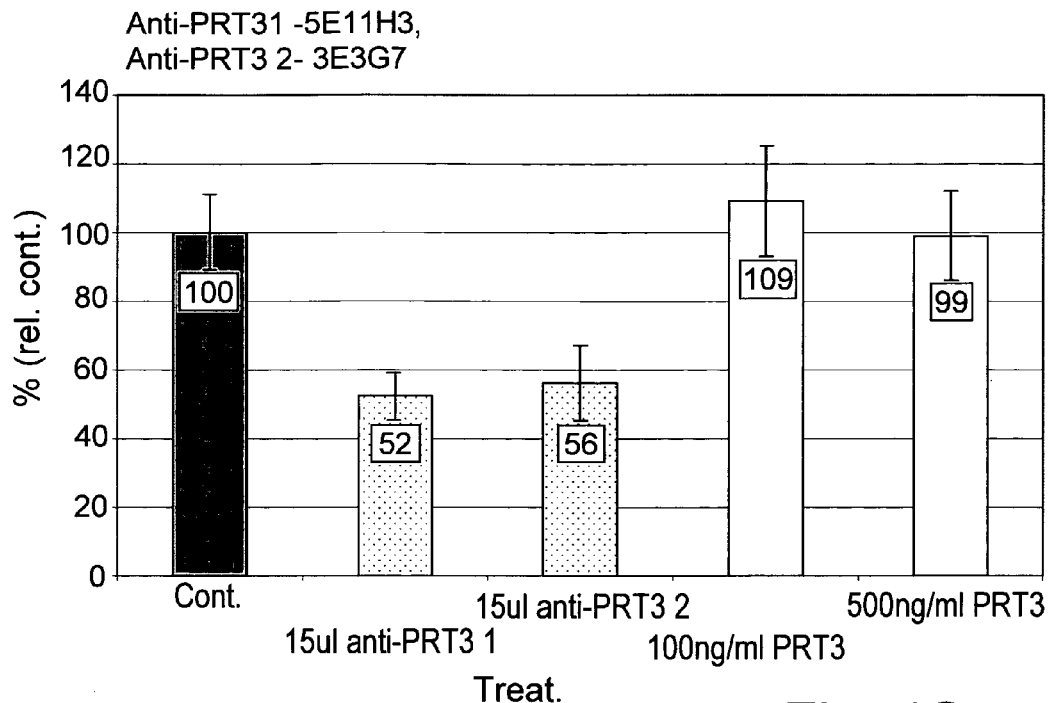
Figure 4D:
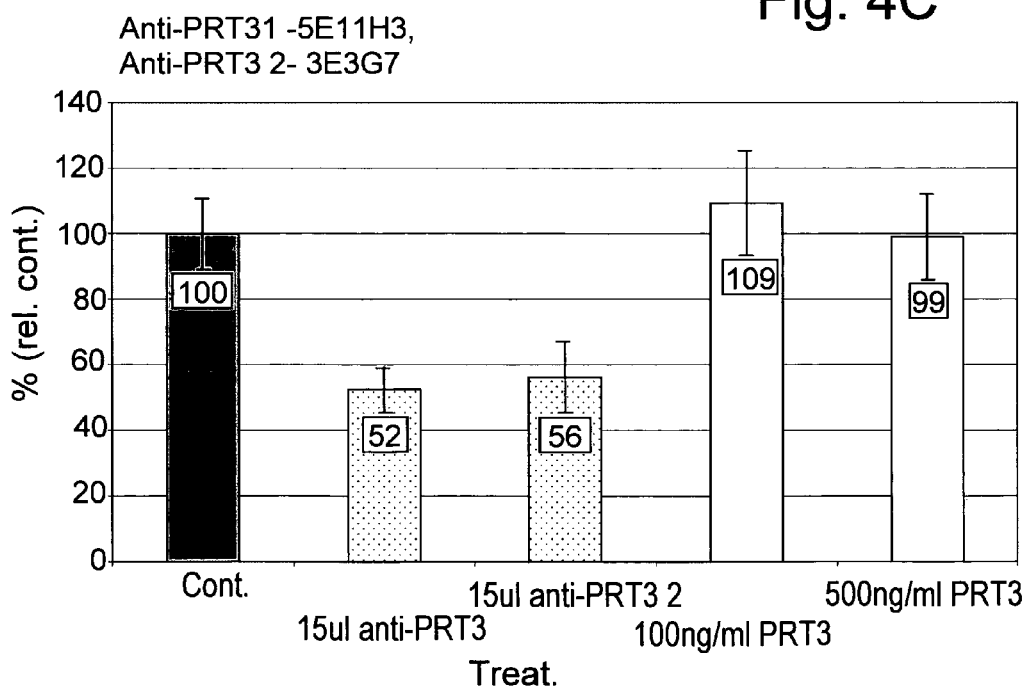

The results are shown in FIGS. 7A-7F. Essentially, after 24 hours of treatment and 24-hour incubation with Resazurin, cell viability in cells from a male) was reduced to 36%, in cultures treated with 5E11H3 and 3E3G7 (FIG. 4A), and cell viability in cells from a female was reduced to 52% and 58%, in cultures treated with 5E11H3 and 3E3G7, respectively (FIG. 4B). A 48-hour treatment with the KTPAF50-specific antibodies reduced cell viability of both male and female cells to an extent similar to the 24-hour treatment in females (FIGS. 4C and 4D).

Figure 4E:
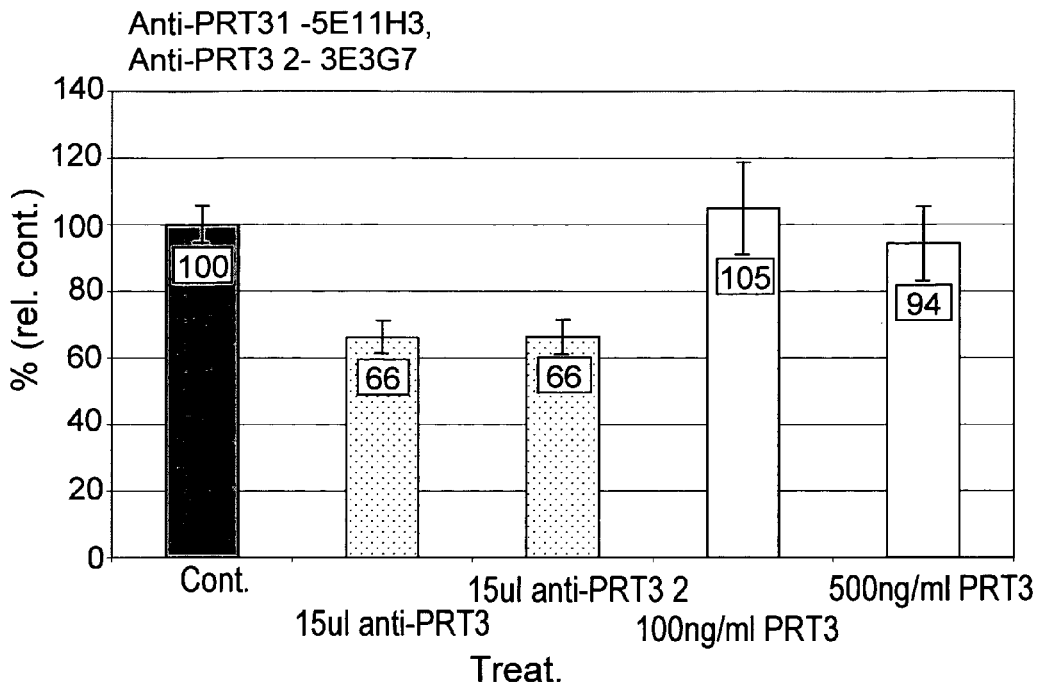
Figure 4F:
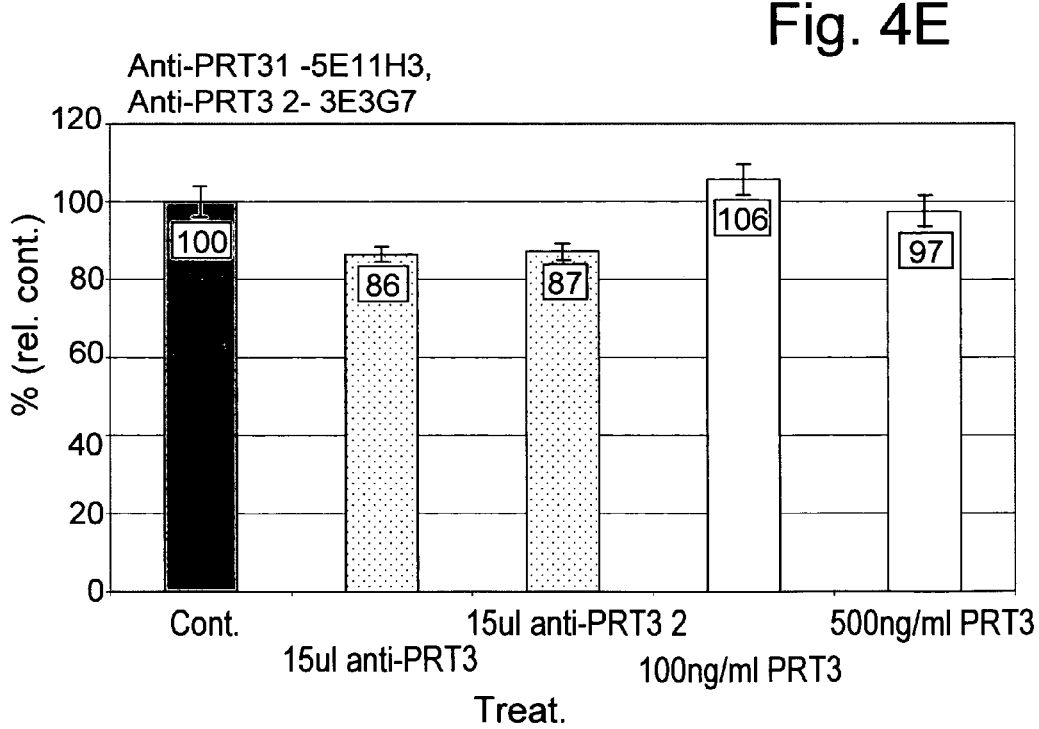

A prolonged treatment with the antibodies (72-hour treatment) did not present further reduction of cell viability (FIGS. 4E and 4F).

The results clearly show that monoclonal antibodies against KTPAF50 can dramatically reduce the viability of C57Bl/6 splenocytes, suggesting that KTPAF50 plays a pivotal role in keeping the viability of mice splenocytes. Neutralizing KTPAF50 activity with specific monoclonal antibodies can serve as a very strong tool for treating autoimmune diseases induced in mice. Similarly, KTPAF50-specific monoclonal antibodies shall be used in human clinical trials.

Example 5

Further to the treatment with KTPAF50 antibodies, the cells were evaluated for the presence of KTPAF50 in the supernatant using an ELISA assay.

Procedure:
1. The 24 hrs control samples from section A (step 4 under procedure) were loaded onto a Maxisorp immunoplates, (Maxisorp #442404). 100 µl in each well in triplicates. As a zero reference, Karyotyping medium was also loaded in triplicates. For quantification, serial dilutions of PRT3 were also loaded (2000 to 63 pg/ml). Plate incubated at 4° C. overnight.
2. After the incubation the plate was washed 4 times using a multi-pipette with 300 µl 0.05% TW-20 (Amresco #0777-1L) in PBS.
3. The plate was blocked using 5% BSA (MP biomedicals #160069) in PBS. 300 µl was loaded in each well. Incubation at R.T. for 1 hour with shaking.
4. The plate was washed as described in step 2.
5. PRT3 polyclonal antibody (affinity purified) was diluted 1:250 in diluent (0.05% TW-20, 0.1% BSA in PBS). 100 µl of the antibody was loaded in each well. Plate incubated at R.T. for 2 hours with shaking.
6. The plate was washed as described in step 2.
7. Goat anti-rabbit HRP conjugate antibody (Cell signaling, 7074) was diluted 1:200 in diluent. 100 µl of the HRP conjugate was loaded each well. Plate incubated for 30 min. at R.T. with shaking.
8. The plate was washed as described in step 2, only with 5 washings instead of 4.
9. 100 µl TMB (Millipore™, ES001-500 ML) was loaded in each well, 50 µl 2N $H_2SO_4$ (Frutarom, 5552540) was loaded after color development to stop the reaction.
10. Plate was read in a microplate reader at 450 nm.

The results are presented in FIG. 5, and confirm the presence of mKTPAF50 in the supernatant.

Example 6

Effect of Monoclonal KTPAF50 Antibodies on Human Monocytes

The effects of KTPAF50 antibodies on human monocytes were analyzed with respect to cell viability, cytokine expression, presence of the KTPAF50 protein in the supernatant and cell morphology.

A. Cell Viability was Tested Using the Resazurin Assay.

Procedure:
1. Human Peripheral Blood Mononuclear Cells (HPBMC) (Lonza #CC-2702) were thawed according to official protocol (See Appendix B) and cultured in Peripheral blood Karyotyping medium (Biological industries #01-201-1B).
2. The cells were divided in two F96 MicroWell™ Plates (Nunc #167008). In each plate 4×5 wells were loaded with 50,000 cells in 200 µl Karyotyping medium. Cells were incubated for 24 hours in 37° C., 5% $CO_2$.
3. After incubation the following treatments were added to each well in quadruplicates:
   a. Control (anti-p53 antibody [Santa Cruz CS-65334]-10 µl.)
   b. 10 µl of anti-KTPAF50 1 (5E11H3)
   c. 25 µl of anti-KTPAF50 1 (5E11H3)
   d. 10 µl of anti-KTPAF50 2 (3E3G7)
   e. 25 µl of anti-KTPAF50 2 (3E3G7)
4. The first plate was incubated for 24 hours and the second for 48 hours in 37° C., 5% $CO_2$.

After the incubation time, 20 µl of Resazurin (R&D systems #AR002) was added to each well, and fluorescence (530/590 nm) measured using a plate reader at 2, 4 and 24 hours (following 24 hour incubation) or at 2 and 4 hours (following 48 hour incubation). The results are presented in FIGS. 6A-6C and 7A-7B, respectively.

B. Analysis of Change in Cytokine Expression in Medium (Supernatant) Following Treatment with Anti-KTPAF50 Antibodies, Using ELISA Assays.

Procedure:
1. Human Peripheral Blood Mononuclear Cells (HPBMC) (Lonza #CC-2702) were thawed according to the thawing protocol (see above) and were cultured in Peripheral blood Karyotyping medium (Biological Industries 01-201-1B).
2. The cells were divided to four 6 Well Multidishes Plates (Nunc #140675). In each well 1M cells were loaded in 2 mL Karyotyping medium. Cells were incubated for 24 hours in 37° C., 5% $CO_2$.
3. After incubation the following treatments were added to each well:
   a. Control
   b. 100 µl of anti-KTPAF50 1 (5E11H3)
   c. 10 µl of anti-KTPAF50 2 (3E3G7)
   d. 100 ng/ml KTPAF50
   e. 500 ng/ml KTPAF50
   f. 1000 ng/ml KTPAF50
4. The plates were incubated for 24, 48, 120 and 144 hours in 37° C., 5% $CO_2$.
5. After incubation, the plates were put on ice and the samples were collected and centrifuged at 300 G for 10 minutes. The medium (supernatant) was taken for the ELISA assays.
6. Samples were loaded onto Maxisorp immunoplates (Nunc #442404) for ELISA assay. The following ELISA kits were used for testing the respective cytokines, according to the manufacturer's instructions (TDS protocol, see above).
   a. Human TNF-alpha (eBioscience™ #88-7346). Samples diluted 1:10
   b. Human IFN-gamma (eBioscience™ #88-7316). Samples diluted 1:10
   c. Human IL-10 (eBioscience™ #88-7106). Samples diluted 1:6
   d. PRT-3. Samples not diluted TNF-α expression was unchanged upon anti-KTPAF50 treatment for 24- or 48-hour treatments (FIGS. 8B-8C), but it was significantly reduced upon 120-hour treatment (FIG. 8D) and in the 144-hour treatment, a reduction occurred using the antibody 5E11H3 (FIG. 8E).

IFN-γ expression was reduced following anti-KTPAF50 treatment, and this reduction was amplified over time (FIGS. 9B-9E).

IL-10 expression was suppressed upon anti-KTPAF50 treatment (FIGS. 10A-10D).

These results strongly demonstrate that KTPAF50-specific antibodies can downregulate human pro-inflammatory cytokines secreted from human peripheral white blood cells, such as TNF-α and IFN-γ. Thus, the monoclonal antibodies provided herein are a potential drug candidate to treat human autoimmune disease, graft rejections, and other conditions alike.

C. Analysis of KTPAF50 Presence in the Medium using an ELISA Assay.

Procedure

1. Two control samples from section B (step 6 under procedure) were loaded onto a Maxisorp immunoplates, (Maxisorp #442404). 100 μl in each well in triplicates. As a zero reference, Karyotyping medium was also loaded in triplicates. Plate incubated at 4° C. overnight.
2. After the incubation the plate was washed 4 times using a multi-pipette with 300 μl 0.05% TW-20 (Amresco #0777-1L) in PBS.
3. The plate was blocked using 5% BSA (MP Biomedicals #160069) in PBS. 300 μl was loaded in each well. Incubation at R.T. for 1 hour with shaking.
4. The plate was washed as described in step 2.
5. KTPAF50 polyclonal antibody (affinity purified) was diluted 1:250 in diluent (0.05% TW-20, 0.1% BSA in PBS). 100 μl of the antibody was loaded in each well. Plate was incubated at room temperature for 2 hours with shaking.
6. The plate was washed as described in step 2.
7. Goat anti-rabbit HRP conjugate antibody (Cell signaling #7074) was diluted 1:200 in diluent. 100 μl of the HRP conjugate was loaded each well. The plate was incubated for 30 min. at room temperature with shaking.
8. The plate was washed as described in step 2, only with 5 washings instead of 4.
9. 100 μl TMB (Milipore #ES001-500 mL) was loaded in each well. After color development 50 μl 2N $H_2SO_4$ (Frutarom #5552540) was loaded to stop the reaction.
10. Plate was read in a microplate reader at 450 nm.

The results are presented in FIG. 11, and confirm the presence of KTAPAF50 in the supernatant.

D. Change in Morphology of Human Monocytes Cells Following Anti-KTPAF50 Treatment, Analyzed Through Light Microscopy Procedure:

1. Human Peripheral Blood Mononuclear Cells (HPBMC) (Lonza #CC-2702) were thawed according to the thawing protocol (see above) and cultured in Peripheral blood Karyotyping medium (Biological Industries 01-201-1B).
2. The cells were divided to four 6 Well Multidishes Plates (Nunc #140675). In each well 1M cells were loaded in 2 mL Karyotyping medium. Cells were incubated for 24 hours in 37° C., 5% $CO_2$.
3. After incubation the following treatments were added to each well:
   a. Control
   b. 100 μl of anti-KTPAF50 1 (5E11H3)
   c. 10 μl of anti-KTPAF50 2 (3E3G7)
   d. 100 ng/ml KTPAF50
   e. 500 ng/ml KTPAF50
   f. 1000 ng/ml KTPAF50
4. The plates were incubated for 120 hours in 37° C., 5% $CO_2$, and visualized using a light microscope (magnification ×100) and a CCD camera (FIGS. 15A-15F).

Human peripheral blood cells treated with PHA proliferate resulting in large clumps of cells. The present results unequivocally show that when PHA treatment is followed by treatment with anti-KTPAF50 monoclonal antibodies, complete inhibition of proliferation of these cells was observed. This makes the antibodies provided herein as a powerful tool for the regulation of proliferation, and as a therapeutic for any condition involving undesired proliferation of cells, such as cancer, diseases that involve inflammatory processes, and the like.

The invention claimed is:

1. A purified antibody or a fragment thereof that specifically binds to the KTPAF50 protein consisting of the amino acid sequence of SEQ ID NO: 2, wherein said purified antibody is produced by a deposited cell line having a CNCM Registration Number selected from CNCM I-4331 and CNCM I-4335.

2. A pharmaceutical composition comprising a purified antibody or a fragment thereof according to claim 1 and a pharmaceutically acceptable carrier, excipient, or diluent.

3. A method for the diagnosis of lung cancer in a subject, said method comprising the steps of:
   a) providing a sample from said subject;
   b) contacting said sample with at least one purified antibody according to claim 1 or a pharmaceutical composition comprising the same; and
   c) detecting the formation of a complex between said at least one purified antibody and its specific antigen;
   whereby the detection of a complex indicates that said subject suffers from lung cancer.

4. The method of claim 3, wherein said sample is a blood sample.

5. A method of inhibiting cytokine expression, said method comprising contacting an effective amount of at least one purified antibody according to claim 1, or a pharmaceutical composition comprising the same, with cells that express cytokines;
   wherein said cytokine is a pro-inflammatory cytokine being selected from the group consisting of TNF-$\alpha$, IFN-$\gamma$ or IL-10.

6. A kit for diagnosis, monitoring treatment efficacy or assessing prognosis of lung cancer, said kit comprising:
   a) at least one purified antibody or a fragment thereof that specifically binds to the KTPAF50 protein consisting of the amino acid sequence of SEQ ID NO: 2, wherein said at least one purified antibody is produced by a deposited cell line having a CNCM Registration Number selected from CNCM I-4331 and CNCM I-4335;
   b) at least one reagent necessary for detecting the recognition of KTPAF50 by said purified antibody; and
   c) instructions for carrying out the detection of the presence of KTPAF50 in a sample.

* * * * *

SEQUENCE LISTING

<160> NUMBER OF SEQ ID NOS: 7

<210> SEQ ID NO 1
<211> LENGTH: 50
<212> TYPE: PRT
<213> ORGANISM: Homo sapiens

<400> SEQUENCE: 1

Leu Arg Arg Arg Glu Gln Ala Glu Arg Gly Ser Arg Arg Cys Ala Ile
1               5                   10                  15

Ala Gly Glu Glu Arg Ala Met Leu Ser Pro Ser Pro Leu Pro Glu Thr
            20                  25                  30

Pro Phe Ser Pro Glu Lys Gly Ala Ala Phe Ser Pro Ile Tyr Pro Arg
        35                  40                  45

Arg Lys
    50

<210> SEQ ID NO 2
<211> LENGTH: 74
<212> TYPE: PRT
<213> ORGANISM: Homo sapiens

```
<400> SEQUENCE: 2

Met Pro Gly His Ser Arg Leu Leu Ser Ile Leu Val Ser Gly Leu Cys
1               5                   10                  15

Val Val Gly Ser Ser Ile Gly Val Leu Arg Arg Glu Gln Ala Glu
            20                  25                  30

Arg Gly Ser Arg Arg Cys Ala Ile Ala Gly Glu Glu Arg Ala Met Leu
            35                  40                  45

Ser Pro Ser Pro Leu Pro Glu Thr Pro Phe Ser Pro Lys Gly Ala
    50                  55                  60

Ala Phe Ser Pro Ile Tyr Pro Arg Arg Lys
65                  70

<210> SEQ ID NO 3
<211> LENGTH: 14
<212> TYPE: PRT
<213> ORGANISM: Homo sapiens

<400> SEQUENCE: 3

Glu Lys Gly Ala Ala Phe Ser Pro Ile Tyr Pro Arg Arg Lys
1               5                   10

<210> SEQ ID NO 4
<211> LENGTH: 36
<212> TYPE: PRT
<213> ORGANISM: Homo sapiens

<400> SEQUENCE: 4

Leu Arg Arg Arg Glu Gln Ala Glu Arg Gly Ser Arg Arg Cys Ala Ile
1               5                   10                  15

Ala Gly Glu Glu Arg Ala Met Leu Ser Pro Ser Pro Leu Pro Glu Thr
            20                  25                  30

Pro Phe Ser Pro
            35

<210> SEQ ID NO 5
<211> LENGTH: 14
<212> TYPE: PRT
<213> ORGANISM: Homo sapiens

<400> SEQUENCE: 5

Leu Arg Arg Arg Glu Gln Ala Glu Arg Gly Ser Arg Arg Cys
1               5                   10

<210> SEQ ID NO 6
<211> LENGTH: 16
<212> TYPE: PRT
<213> ORGANISM: Homo sapiens

<400> SEQUENCE: 6

Pro Glu Lys Gly Ala Ala Phe Ser Pro Ile Tyr Pro Arg Arg Lys Cys
1               5                   10                  15

<210> SEQ ID NO 7
<211> LENGTH: 15
<212> TYPE: PRT
<213> ORGANISM: Homo sapiens

<400> SEQUENCE: 7

Cys Ala Ile Ala Gly Glu Glu Arg Ala Met Leu Ser Pro Ser Pro
1               5                   10                  15
```